(12) United States Patent
Boit et al.

(10) Patent No.: US 11,945,835 B2
(45) Date of Patent: *Apr. 2, 2024

(54) METHOD FOR PRODUCING D-ALLULOSE CRYSTALS

(71) Applicant: ROQUETTE FRERES, Lestrem (FR)

(72) Inventors: Baptiste Boit, La Gorgue (FR); Geoffrey Lacroix, Lille (FR); Laurent Rossi, Arras (FR)

(73) Assignee: ROQUETTE FRERES, Lestrem (FR)

( * ) Notice: Subject to any disclaimer, the term of this patent is extended or adjusted under 35 U.S.C. 154(b) by 138 days.

This patent is subject to a terminal disclaimer.

(21) Appl. No.: 16/471,753

(22) PCT Filed: Jan. 5, 2018

(86) PCT No.: PCT/FR2018/050026
§ 371 (c)(1),
(2) Date: Jun. 20, 2019

(87) PCT Pub. No.: WO2018/127668
PCT Pub. Date: Jul. 12, 2018

(65) Prior Publication Data
US 2019/0330253 A1    Oct. 31, 2019

(30) Foreign Application Priority Data
Jan. 5, 2017  (FR) ...................... 17 50103

(51) Int. Cl.
| | |
|---|---|
| *C07H 3/02* | (2006.01) |
| *A23L 27/30* | (2016.01) |
| *B01D 61/02* | (2006.01) |
| *B01D 61/04* | (2006.01) |
| *C07H 1/06* | (2006.01) |

(52) U.S. Cl.
CPC .............. *C07H 3/02* (2013.01); *A23L 27/33* (2016.08); *B01D 61/027* (2013.01); *B01D 61/04* (2013.01); *C07H 1/06* (2013.01); *B01D 2311/04* (2013.01); *B01D 2311/2676* (2013.01)

(58) Field of Classification Search
CPC ... C07H 1/06; C07H 1/00; C07H 3/02; B01D 61/027; B01D 2311/04; B01D 2311/2676; B01D 61/04; A23L 27/33
USPC ...................................... 536/127
See application file for complete search history.

(56) References Cited

U.S. PATENT DOCUMENTS

| | | | | |
|---|---|---|---|---|
| 8,524,888 B2 * | 9/2013 | Lee | ...................... | C07H 3/02 536/127 |
| 2005/0211239 A1 * | 9/2005 | Koivikko | ................ | C13B 20/12 210/659 |
| 2016/0281076 A1 | 9/2016 | Lanos et al. | | |
| 2016/0331014 A1 | 11/2016 | Perera | | |
| 2017/0208849 A1 | 7/2017 | Boit et al. | | |

FOREIGN PATENT DOCUMENTS

| | | | | |
|---|---|---|---|---|
| CN | 103059071 A | * | 4/2013 | ............... C07H 1/06 |
| CN | 103 333 935 A | | 10/2013 | |
| CN | 104 447 888 A | | 3/2015 | |
| CN | 103 059 071 B | | 3/2016 | |
| EP | 1 860 195 A1 | | 11/2007 | |
| FR | 3 016 628 A1 | | 7/2015 | |
| JP | 2001-354690 A | | 12/2001 | |
| JP | 3399576 B2 | | 4/2003 | |
| JP | 4761424 B2 | | 8/2011 | |
| KR | 10-0287306 B1 | | 10/1994 | |
| WO | 2011/119004 A2 | | 9/2011 | |
| WO | WO 2011/119004 A2 | * | 9/2011 | ............. A23L 1/236 |
| WO | 2015/032761 A1 | | 3/2015 | |
| WO | 2015/094342 A1 | | 6/2015 | |
| WO | 2016/012853 A1 | | 1/2016 | |
| WO | 2016/064087 A1 | | 4/2016 | |

OTHER PUBLICATIONS

Torres, Bitesizebio, 2016, pp. 1-5.*
Takeshita et al., "Mass Production of D-Psicose from D-Fructose by a Continuous Bioreactor System Using Immobilized D-Tagatose 3-Epimerase," Journal of Bioscience and Bioengineering, 2000, vol. 90, No. 4, pp. 453-455.
Salehi, Fakhreddin, "Current and future applications for nanofiltration technology in the food processing," Food and Bioproducts Processing, 2014, vol. 92, pp. 161-177.
Mar. 7, 2018 International Search Report issued in International Patent Application No. PCT/FR2018/050026.
Hinkova, A. et al., "Membrane Filtration in the Sugar Industry" Chemical Papers, May 2000, vol. 54, pp. 375-382.
Kim et al., "An Improved Analytical Method for the Determination of Qualitative and Quantitative Characteristics of Di—and Trisaccharides in Honey using Gc and Gc/MS", Korean J. Food Sci. Technol., vol. 47, No. 1, pp. 27-36 (2015).
H.E. van Dam, "The Conversion of Fructose and Glucose in Acidic Media: Formation of Hydroxymethylfurfural", Starch 28 (1986) Nr. 3, S. 95-101.
Oct. 31, 2023 Third Party Observation issued in Korean Patent Application 10-2019-7019099.

* cited by examiner

*Primary Examiner* — Ganapathy Krishnan
(74) *Attorney, Agent, or Firm* — Oliff PLC

(57) ABSTRACT

A new method for producing D-allulose crystals that allows for a continuous production process and ensures a high yield. Also, new D-allulose crystals. Further, the use of a nanofiltration unit in a method for producing D-allulose crystals to improve the yield and/or quality of the resulting crystals.

15 Claims, 11 Drawing Sheets

» Feret$_{min}$ / Feret$_{max}$

METHOD FOR PRODUCING D-ALLULOSE CRYSTALS

FIELD OF THE INVENTION

The invention relates to a novel process for producing D-allulose crystals which makes it possible to work continuously and to obtain a high yield. A subject of the invention is also novel D-allulose crystals. Another subject of the invention relates to the use of a nanofiltration unit in a process for producing D-allulose crystals in order to improve the yield thereof and/or the quality of the crystals obtained.

PRIOR ART

D-allulose (or D-psicose) is a rare sugar which has a sweetening power equal to 70% of that of sucrose. Contrary to the latter, D-allulose does not cause weight gain since it is not metabolized by human beings. It has a very low calorie content (0.2 kcal per gram) and it thus prevents an increase in body fat. Furthermore, studies have shown that D-allulose is non-cariogenic, or even anti-cariogenic. Thus, these properties have recently generated a very great deal of interest from the food and pharmaceutical industries.

Even though it is possible to obtain D-allulose chemically, for example by reacting an aqueous solution of glucose in an acidic medium in the presence of an ammonium molybdate catalyst, D-allulose is generally obtained enzymatically, by reacting an aqueous solution of D-fructose with a D-psicose epimerase as described, for example, in application WO 2015/032761 A1 in the name of the applicant. In the two cases, the reaction is not total. For example, the amount of D-fructose converted into D-allulose after epimerization is generally less than 30%.

Thus, at the end of the epimerization reaction, it is necessary to carry out a step of separating the D-allulose, in order to increase the richness of the resulting D-allulose composition. In order to carry out this separation, chromatography of the composition resulting from the epimerization reaction is very generally carried out, for example by continuous chromatography of simulated mobile bed type.

Document JP 2001354690 A describes a process for producing a D-allulose syrup starting from a mixture of fructose and D-allulose, said process comprising a separation step consisting of a step of continuous chromatography using a particular sequence of samples of the various products of the mixture. A fraction rich in D-allulose (the D-allulose richness of which can reach 98%) and a reaction rich in fructose are recovered. The recovery yield in the fraction rich in D-allulose is 96%.

At the end of the abovementioned separation steps, liquid compositions rich in D-allulose are obtained. Thus, these liquid compositions, generally called syrups, are used for the production of food or pharmaceutical products.

By way of example, application WO 2015/094342, also in the name of the applicant, describes the production of solid food products comprising a D-allulose syrup, comprising from 50% to 98% of D-allulose and a native protein. It is mainly in this syrup form that various companies have to date announced the marketing of D-allulose.

D-allulose is also sold in powder form. However, as explained below, the productions of said powders can be quite complex.

It is possible to produce powders using for example spray-drying techniques. However, the spray-dried powders, the composition of which depends on the raw material that is spray-dried, generally comprise large amounts of impurities. Moreover, these spray-dried powders are weakly crystalline; they are very hygroscopic and this thus causes water resistance problems. This also creates generally more substantial caking phenomena.

Because of these difficulties, the spray-drying of D-allulose has been described very little in the literature. By way of example, mention may be made of document EP 1 860 195 which describes the spray-drying of a mixture comprising D-allulose and D-allose. With regard to the enantiomer of D-allulose, L-allulose, mention may be made of document JP 4761424 which describes the spray-drying of a cooked mass of D-allulose.

It is also possible to produce powders by means of granulation techniques, as described for example in application WO 2016/012853, in the name of the applicant.

Another form of powders concerns crystals obtained by crystallization of a stock solution of D-allulose.

A process for producing D-allulose crystals has been described in document CN 104447888 A. This document describes more particularly in the examples a process comprising a step of producing a solution of D-allulose from glucose using a molybdate catalyst, and then a step of decoloring this solution using active carbon and then filtering in order to remove the active carbon, a step of deionizing by electrodialysis, a step of separating by continuous chromatography so as to form a solution of D-allulose having a purity ranging from 70% to 90%, a step of concentrating said solution so as to obtain a concentrated solution of D-allulose, followed by a step of crystallization from ethanol so as to obtain a crystalline D-allulose product having a limited purity, at the very most of 99%. No crystallization yield is indicated in said document.

Another crystallization process has also been described in document WO 2011/119004 in the name of CJ Cheiljedang, in which the crystallization yield is about 50%. This process for producing D-allulose crystals comprises a step of providing a solution of D-allulose, a step of purifying this solution, a step of concentrating the solution of D-allulose so as to provide a stock solution and a step of crystallization of this stock solution, in which the crystallizing step is carried out while maintaining the stock solution in its metastable zone. The purifying step described in said document is a step of separating by chromatography, which makes it possible to separate the D-allulose from the fructose. However, said document acknowledges that the production of powders in crystal form is difficult to carry out:

First of all, this crystallization is difficult to control, in which it is specified that the crystallization must be carried out with care, by continuous observation of the crystals, while also measuring the concentration of the supernatant, this being in order to regulate the temperature in the crystallizer. However, said document is silent with regard to the reasons for which it is difficult to perform this crystallization.

Furthermore, the crystals obtained have a size of less than 200 µm and art thus, because of their small size, difficult to separate from the mother liquors from crystallization, during centrifugation. The crystals recovered are also difficult to handle during subsequent use.

Document WO 2016/064087, also in the name of CJ Cheiljedang, also describes, in Example 3, a process for producing D-allulose crystals in which a stock solution is introduced into a crystallizer at four distinct moments. Between each introduction, four heating and cooling cycles are carried out, thereby resulting in a process which lasts more than 80 hours. In comparison with the process described in document WO 2011/119004, the crystallization yield is not improved (it is 52.8%). The crystals obtained have a larger mean size (mean aperture equal to 374 µm). However, the crystals obtained exhibit impurities. Moreover, the crystals which are sold by the company CJ Cheiljedang are needle-shaped, which results in a flow that is not entirely satisfactory.

It appears from the aforementioned that many problems still remain in the production of D-allulose crystals.

First of all, the overall yield of D-allulose crystals is excessively low. The term "overall yield of D-allulose crystals" is intended to mean the ratio, expressed as dry mass, of the mass of D-allulose crystals obtained to the mass of D-fructose introduced. This low yield, of about 15% relative to the D-fructose, is essentially linked to the yields of the epimerization (less than 30%) and crystallization (generally of about 50%) steps.

In order to improve the yield of the processes, it is thus imperative to carry out "recycling steps". The term "recycling step" in a process is intended to mean the re-use, in a prior step of the procedure, of a fraction of product obtained during a separating step. In the present application, the term "separating step" is intended to mean any step which makes it possible to separate a composition comprising a product A and a product B into at least a first fraction which is richer in product A and a second fraction which is richer in product B. The fraction may be in any form, for example in solid form, in liquid form, or even in the form of a solid suspension in a liquid. A separating step may be of any type, for example a chromatography step, in which the liquid composition is separated into at least two liquid fractions, or else a crystallizing step wherein a liquid composition is separated into a solid fraction and a liquid fraction.

Steps in which fructose-rich fractions are recycled have already been described with a view to improving the yield of the process for producing D-allulose syrups. In particular, document JP2001354690 A previously cited describes the recycling of the fructose-rich fraction obtained during the chromatography step in order to subject it to the epimerizing step. This makes it possible to improve the yield of D-allulose in the form of a liquid composition.

It is in seeking to apply the teachings of said document in a process for producing D-allulose crystals (such as, for example, that described in document WO 2011/119004), that the applicant has been able to note that they were not simply transposable.

This is because, when the recycling of the fructose-rich fraction is carried out (see FIG. 1), the applicant was able to note that the stock solution obtained becomes increasingly difficult to crystallize. After a certain time, this crystallization becomes impossible, as demonstrated in the Examples section.

Moreover, still with the aim of improving the overall yield of D-allulose crystals of the process, the applicant has also attempted to perform a recycling of the mother liquors from crystallization (that is to say of the solution rich in D-allulose that is obtained after separating the crystals obtained during the crystallizing step) by mixing them with a D-allulose composition so as to form, after concentration, a new stock solution (see FIG. 2). It has been able to note (see Examples section) that this recycling of the mother liquors causes the same difficulties, this being even more rapidly than in the case of the recycling of the fructose-rich fraction.

In these two cases previously described, interruptions in the production of the D-allulose crystals must thus be made.

Moreover, the applicant has been able to note that, even without carrying out recyclings, when transposing the teachings described above into a continuous industrial process for manufacturing D-allulose crystals, "instabilities" are observed. These instabilities result in massecuites of crystals which inexplicably have a variable appearance during the process. This is particularly bothersome since the massecuites of crystals can be centrifugable and then non-centrifugable at certain moments, without it being possible to make any prediction, a priori, of the behavior thereof. There is then a need to re-melt the massecuites obtained if it is desired to re-use them in the process, and this makes the process not very practical and less economical.

In point of fact, with a view to accelerating the industrial development of D-allulose, which is today mainly sold in syrup form, it is imperative, on the industrial scale, to be able to carry out a continuous and stable process for producing D-allulose crystals, in order to be able to supply them at a competitive price.

After a great deal of research, the applicant has succeeded in obtaining a process for producing D-allulose crystals in which the problems mentioned above can be solved.

Because of an improved process stability, the production of the crystals does not require any systematic control as for example indicated in document WO 2011/119004, which makes possible the implementation of a continuous process for producing D-allulose crystals.

Moreover, since the process of the invention also allows numerous recycling steps, the yield of the process can be greatly increased.

By carrying out a great deal of research, the applicant has been able to note that, in a process for producing D-allulose crystals, particular impurities form during the various steps of the process for preparing the stock solution. These impurities have, to the applicant's best knowledge, never been reported in the literature. It has been possible for the applicant to identify them by using a particular gas chromatography (GC) technique. Without being bound to any theory, the applicant thinks that these impurities are D-allulose dimers which form by condensation throughout the process.

The applicant has also been able to show that these D-allulose dimers, contrary to other impurities such as glucose or D-fructose, have a very significant anti-crystallizing effect.

Surprisingly, the applicant has succeeded, by carrying out a process for producing D-allulose crystals in which a particular separating step is carried out, in eliminating this problem of difficult crystallization of D-allulose. This separating step consists of a nanofiltration step, which makes it possible to remove these anti-crystallizing impurities.

This novel process provides a major advance for the industrial development of D-allulose crystals since it makes it possible to achieve an overall yield exceeding 25% relative to the D-fructose introduced, advantageously exceeding 50%, or even exceeding 65%. This makes it possible to envision the production of D-allulose crystals at a competitive price and also the commercial development of such crystals on a larger scale.

Moreover, the applicant has noted that the presence of these impurities is a factor which influences the shape of the crystals, in particular when it is sought to produce large crystals, in particular when their mean size exceeds 200 µm.

During its research, the applicant has also succeeded in producing novel D-allulose crystals using a specific crystallization process using, among the production steps, the nanofiltration step mentioned above. These crystals, which are another aspect of the present invention, have in particular the particularity of comprising a very low mass percentage of D-allulose dimer. The crystals obtained can also have a different shape and an improved flow. These shape and flow properties are directly linked to the fact that the dimers are present in the crystals in very small amounts. Conversely, when it is desired to produce large crystals, the considerable presence of D-allulose dimers in the stock solution during the crystallization results in D-allulose crystals comprising considerable amounts of these dimers; moreover, the elongation of these crystals so as to form needles is observed. In point of fact, these needle-shaped crystals can exhibit a lesser flow than the crystals of the invention.

SUMMARY OF THE INVENTION

The invention thus relates to a process for producing D-allulose crystals, comprising:
- a step of providing a composition rich in D-allulose;
- a step of concentrating said solution so as to form a stock solution to be crystallized;
- a step of crystallizing the stock solution so as to form D-allulose crystals and mother liquors;
- and at least one nanofiltration step, said step taking place in a step prior to the step of concentrating the composition rich in D-allulose.

As mentioned above, the applicant has been able to note that, systematically, in a process for producing D-allulose crystals, particular impurities form during the process. Said impurities have, to the applicant's best knowledge, never been reported in the literature. This is explained by the fact that, with the high performance liquid chromatography (HPLC) technique conventionally used to measure the purity of D-allulose, these impurities are not detected on the chromatograms (see FIGS. 7 and 8). It is by using a gas chromatography technique that the applicant has been able to detect the presence thereof (see FIGS. 9 and 10).

It has been possible for the applicant to identify these impurities as being D-allulose dimers. The applicant has also been able to show that these dimers, contrary to other impurities such as glucose or D-fructose, have a very significant anti-crystallizing effect. In point of fact, since these D-allulose dimers form during the process, their presence can limit the yield of a continuous process for producing D-allulose crystals by purely and simply preventing this crystallization, by forming non-centrifugable massecuites, if the amounts of these dimers are too high. Moreover, in an industrial and continuous process for producing D-allulose crystals wherein numerous successive steps are carried out, the amount of these purities can vary over time. This makes the process unstable over time, since the massecuites are sometimes centrifugable, sometimes non-centrifugable.

It is to the applicant's credit to have identified these specific impurities and to have succeeded in removing them, by carrying out a separating step consisting in at least partly separating these D-allulose dimers by nanofiltration.

By means of the process of the invention which makes the crystallizing step very stable, it is then possible to carry out the process continuously, but also to drastically increase the overall yield of D-allulose crystals. This is allowed by the fact that it is possible to provide a stock solution of D-allulose having a very small amount of D-allulose dimers, this being by virtue of the abovementioned nanofiltration step.

It is also to the applicant's credit to have succeeded in providing novel D-allulose crystals using this stock solution, in a particular crystallization process which also limits the in situ formation of said dimers. This results in crystals of which the mass percentage of D-allulose dimers is lower than those of the prior art. Another subject of the invention thus relates to D-allulose crystals comprising a mass content of D-allulose dimer, determined by gas chromatography (GC), of less than 0.5%.

With regard to the crystals described in document WO 2011/119004 A2, since they have a very fine size, they are difficult to separate from the crystallization mother liquors. The mother liquors comprise large amounts of D-allulose dimers and the dimer content in the crystals recovered after separation is therefore high, much higher than that of the crystals of the invention.

Moreover, comparative example 3 of the present application (see example sections) demonstrate that even by further improving the process described in this document, the applicant did not manage to obtain the crystals of the invention.

As for the crystals described in document WO 2016/064087, they exhibit impurities, which may be D-allulose dimers in amounts greater than the crystals of the invention. Without being bound by any theory, the presence of these dimers may be explained by the fact that the D-allulose solution is kept on the heat before being introduced into the crystallizing dish, i.e. for a period of time reaching 60 hours. Furthermore, this document is totally silent with regard to how the stock solution is prepared, in particular with regard to the conditions of the concentration step. In point of fact, as emerges in the remainder of the description, the choice of the conditions of the crystallization and concentration steps have an essential impact on the amount of D-allulose dimers formed. Thus, the choice of these conditions makes it possible to limit the amounts of dimers formed during the process and thus to decrease the D-allulose dimer contents in the D-allulose crystals obtained. Since the choice of the conditions of the steps for preparing the stock solution have an essential impact on the amount of D-allulose dimers therein, this document describes neither the stock solution of use in the preparation of the crystals of the invention, nor the crystals themselves.

Document EP 1 860 195 describes tubular-type complex crystalline compositions of D-allose and D-allulose in which the D-allulose is in the minority, and not D-allulose crystals.

For the crystalline compositions obtained by crystallization from ethanol that are described in document CN 104447888 A, this document is silent with regard to the numerous conditions of the process for producing the crystalline compositions and in particular with regard to the step for concentrating the stock solution. It is in this respect impossible to reproduce these crystalline composition production tests. However, it is of use to note that the crystallization must be specifically carried out in an organic solvent such as ethanol. However, it is known that a crystallization in this type of solvent is used only if necessary. Indeed, water which is generally preferred for obvious cost and environmental reasons. An organic solvent selected (ethanol in the case of D-allulose), although more expensive and entailing difficulties for reprocessing it, has the advantage of facilitating the crystallization, making possible a crystallization that would be possible from water. This therefore confirms that the stock solution of D-allulose comprises large amounts of impurities of D-allulose dimer type and this may be explained by the fact that no particular precaution for the various steps of preparing the stock solution appear to have been taken (in particular no condition is indicated for the concentration step). Moreover, in terms of purification, crystallization from ethanol can be less efficient for obtaining D-allulose crystals of high purity than crystallization from water (when this is possible) since these dimers, of chemical nature close to D-allulose, are also sparingly soluble in ethanol and likewise precipitate. Finally, other impurities, which are also numerous, are found in the crystalline compositions, as demonstrated by the low purities obtained in this document.

Crystalline compositions obtained by crystallization from ethanol are also described in the publication by Takeshita et al. (*Mass production of D-psicose from D-fructose by a continuous bioreactor system using immobilized D-tagatose 3-epimerase*, Journal of Bioscience and Bioengineering, Vol. 90 No. 4, January 2000, pages 453-455). This document concentrates on the first step of preparing the D-allulose and not on the production of the D-allulose crystals which here again have very little detail. Since the choice of the conditions of the steps for preparing the stock solution have an essential impact on the amount of D-allulose dimers therein, this document describes neither the stock solution of use in the preparation of the crystals of the invention, nor the crystals themselves. Moreover, in this document, it is specified that this crystallization is carried out from ethanol in order to facilitate the solidification of the D-allulose, which demonstrates the high amount of non-crystallizing impurities and confirms the impossibility of crystallizing the D-allulose stock solution of this document from water. Moreover, the crystallization in question in this document is in reality merely an uncontrolled "precipitation" by addition of ethanol, inevitably leading to impure solid crystalline compositions.

Other crystalline compositions are also mentioned in document CN 103333935 A, but with no details regarding their preparation, since no condition for preparing the stock solution nor any condition for the crystallization (not even the solvent) are indicated. Moreover, this document does not comprise a preparation test per se. Since the choice of the conditions of the steps for preparing the stock solution have an essential impact on the amount of D-allulose dimers therein, this document describes neither the stock solution of use in the preparation of the crystals of the invention, nor the crystals themselves. Moreover, the low purities of the crystalline compositions obtained (98%) in this document appear to indicate that the crystalline compositions are very impure.

Another subject of the invention also relates to the use of a nanofiltration unit in a circuit for producing D-allulose crystals in order to improve the overall yield of D-allulose crystals.

DETAILED DESCRIPTION OF THE INVENTION

A process for producing D-allulose crystals conventionally comprises:
- a step of concentrating a composition rich in D-allulose so as to provide the stock solution to be crystallized;
- a step of crystallizing the stock solution so as to form D-allulose crystals and mother liquors;
- a step of separating the mother liquors and the D-allulose crystals.

The process of the invention has the particularity of comprising a nanofiltration step.

This nanofiltration step makes it possible to limit the amount of D-allulose dimers in the stock solution provided in the process of the invention. This nanofiltration step takes place in a step prior to the step of concentrating the composition rich in D-allulose. This step thus allows the provision of a stock solution of D-allulose of which the D-allulose dimer content is lower than that obtained from one and the same process not using this nanofiltration step.

In the nanofiltration step, which is essential to the process of the invention, two fractions are formed when a composition of D-allulose is subjected to nanofiltration:
- a permeate, which is poor in D-allulose dimers;
- and also a retentate, which is enriched with D-allulose dimers.

Figure 3:
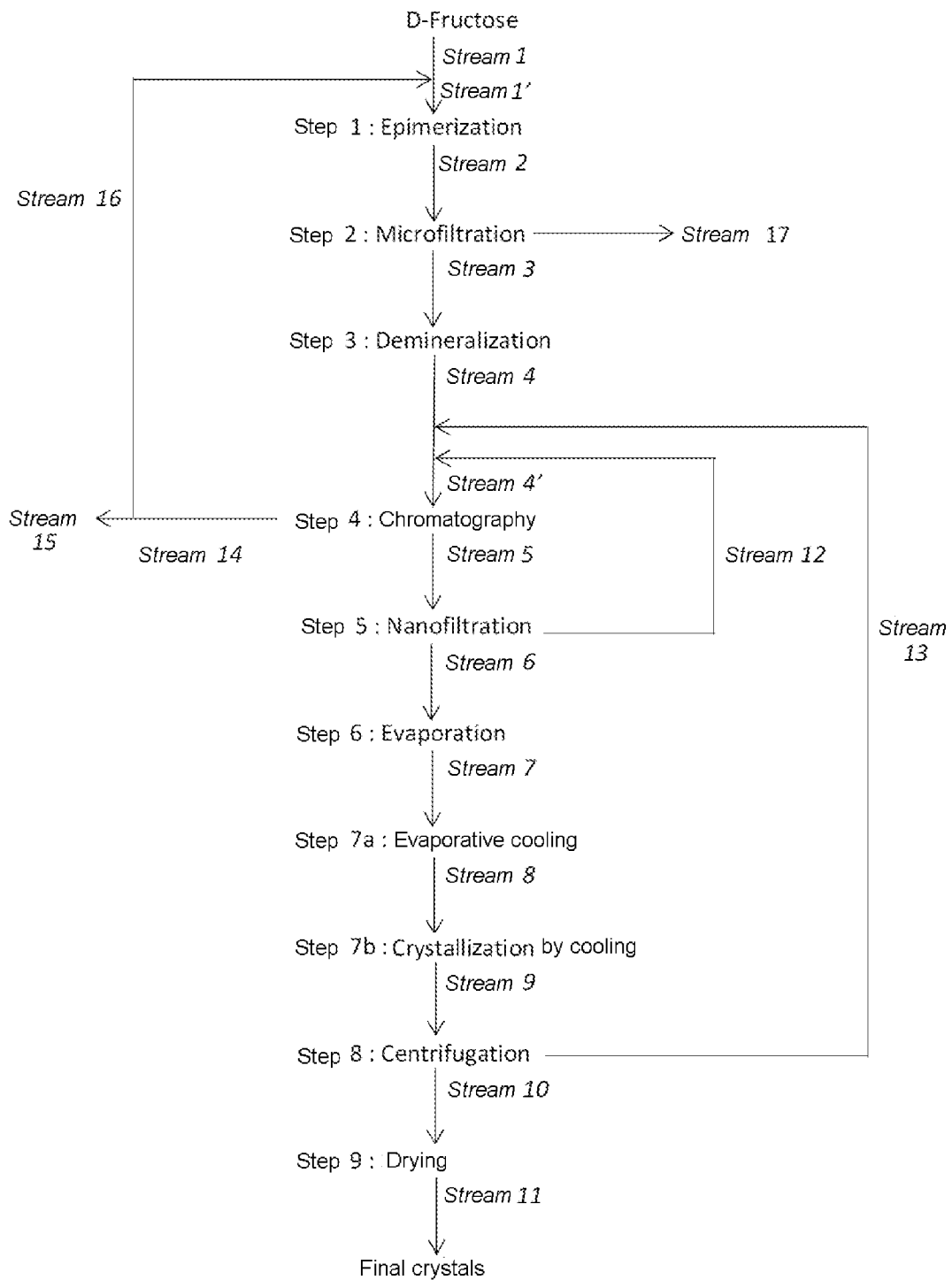
FIG. 3 represents diagrammatically a circuit for producing D-allulose crystals comprising a nanofiltration unit of use in the process of the invention.

In FIG. 3, which represents a circuit for producing crystals that is of use in the process of the invention, Stream 6 represents the permeate and Stream 12 represents the retentate. For illustrative but non-limiting reasons, the Streams indicated in the remainder of the description refer to the streams of the production circuit of this FIG. 3.

The nanofiltration permeate is an intermediate which allows the production of this stock solution. The terms "poor in D-allulose dimers" and "enriched with D-allulose dimers"

are obviously relative to the content of D-allulose oligomers of the composition to be nanofiltered. The term "D-allulose dimer" is intended to mean a compound comprising a D-allulose condensed with at least a second identical or different monosaccharide. These dimers are for example dimers of D-allulose-D-allulose type.

These dimers could be detected by GC and could not be detected during the HPLC analysis, as demonstrated in the examples section. It follows from this that the mass amounts of the various constituents, expressed as dry mass, are in the present application systematically determined by GC. In order to determine the amounts of each of the species in the composition, the sample generally undergoes a treatment step in order to convert the various species present into methoximated trimethylsilyl derivatives. The mass amounts of each of the species are expressed in the present application, unless otherwise mentioned, relative to the total dry mass.

The amounts of glucose, of fructose and of allulose can be determined in a gas chromatograph equipped with an injector heated to 300° C., equipped with a flame ionization detector (FID) heated to 300° C. and equipped with a 40-meter DB1 capillary column, having an internal diameter of 0.18 mm and a film thickness of 0.4 µm, the column temperature being programmed in the following way: from 200° C. up to 260° C. at a rate of 3° C./min, then from 260° C. up to 300° C. at 15° C./min, hold at 300° C. for 5 min.

The term "amount of D-allulose dimers" is intended to mean the difference between the total amount of dimers in a sample, determined by GC, and the amount of the known dimers possibly present, which are glucose-glucose dimers such as maltose and isomaltose. However, the amount of these glucose-glucose dimers is generally very small, or even non-existent. For example, in the stock solution of use in the invention, the mass amount of glucose-glucose dimers is generally less than 0.2%, often less than 0.1%. The same is true for the crystals of the invention.

The possible amount of glucose-glucoses dimers can be determined under the same conditions as those previously described for glucose, fructose and D-allulose:
- by carrying out a hydrolysis of the glucose-glucose dimers of the invention;
- by determining the amount of total glucose in the same chromatogram and under the same conditions, said total glucose comprising the initial glucose termed free and the glucose resulting from the hydrolysis of the glucose-glucose dimers;
- by subtracting, from this amount of total glucose, the amount of initial glucose of the sample.

The total amount of dimers can, for its part, be determined in a gas chromatograph under the same conditions as previously described, with the difference that the column used is a 30-meter DB1 capillary column, having an internal diameter of 0.32 mm and a film thickness of 0.25 µm, and the column temperature is programmed in the following way: from 200° C. up to 280° C. at a rate of 5° C./min, then hold at 280° C. for 6 min, then from 280° C. up to 320° C. at 5° C./min, hold at 320° C. for 5 min.

The method is described in greater detail in the Examples section.

In order to carry out the nanofiltration step of use in the invention, the composition to be nanofiltered is passed through a nanofiltration membrane. It generally has a dry matter content ranging from 5% to 15%.

The temperature of this composition to be nanofiltered can range from 10 to 80° C., generally from 15 to 50° C., often around 20° C.

Those skilled in the art will know how to choose the membrane of use in this separation. This nanofiltration membrane can have a cut-off threshold of less than 300 Da, preferably ranging from 150 to 250 Da. Ideally, the membrane has an $MgSO_4$ rejection rate of at least 98%. It may in particular be a membrane of Dairy DK or Duracon NF1 type manufactured by GE®.

The pressure applied to the membrane can also vary widely and can range from 1 to 50 bar, preferably from 5 to 40 bar, most preferentially from 15 to 35 bar.

This nanofiltration step can be accompanied by a diafiltration phase.

Preferably, the volume concentration factor (VCF) of the nanofiltration ranges from 2 to 20. This volume concentration factor is easily regulated by those skilled in the art.

This nanofiltration step can be carried out continuously.

According to the invention, the step of providing a composition rich in D-allulose can comprise:
- a step of providing a composition comprising D-fructose (Stream 1 or 1');
- an epimerizing step so as to form a composition comprising D-fructose and D-allulose (Stream 2);
- a chromatography step so as to provide a composition rich in D-allulose (Stream 5) and a raffinate, which is a composition rich in D-fructose (Stream 14).

Preferably, the nanofiltration step is carried out between the step of providing the composition rich in D-allulose (Stream 5) and the concentrating step so as to form the stock solution of D-allulose (Stream 7). The step of nanofiltration of said composition rich in D-allulose provides a retentate (Stream 12) and a permeate (Stream 6).

Thus, a variant of the preferred of the invention which comprises:
- a step of providing a composition rich in D-allulose;
- a step of nanofiltration of said composition rich in D-allulose so as to provide a retentate and a permeate;
- a step of recovering the nanofiltration permeate;
- a step of concentrating this permeate so as to provide the stock solution of D-allulose.

In the process of the invention, the nanofiltration step is thus advantageously carried out on the composition rich in D-allulose resulting from the chromatography step, just before the concentrating step which provides the stock solution. It is in this configuration that the process makes it possible to most effectively limit the amount of D-allulose dimers in the stock solution to be crystallized, and thus to most substantially increase the overall yield of D-allulose crystals.

The term "composition rich in D-allulose" is intended to mean generally a composition having, by dry mass, a mass content of D-allulose of greater than 80%, advantageously ranging from 80% to 99%, preferentially from 82% to 98%.

With regard to the permeate obtained, the dry matter content thereof can vary, for example in the range of from 3% to 15%. The permeate can in particular comprise, in addition to the D-allulose, D-fructose and glucose, and also other sugars possibly present. The composition of this filtrate can be very different and depends on the composition to be nanofiltered. At the end of this nanofiltration step, the permeate recovered can comprise, relative to its dry mass, from 0% to 1.2% of D-allulose dimers, example from 0.1% to 1.0%, in particular from 0.15% to 0.5%. The permeate can be subjected to one or more steps such as a step of mixing with an additional product, a separating step, a purifying step, an epimerizing step or a concentrating step.

With regard to the retentate obtained, the dry matter content thereof can also vary widely, for example in the range of from 15% to 40%. It may comprise mainly D-fructose, D-allulose, glucose and D-allulose dimers. According to one variant, the retentate is recovered, optionally mixed with an additional composition of D-allulose, so as to provide, after an optional concentrating step, a D-allulose syrup.

In the preferred variant wherein the composition rich in D-allulose which comprises D-allulose dimers is subjected to a nanofiltration step, the permeate obtained (Stream 6), termed "preferred permeate", preferably comprises, by dry mass:
from 80% to 99% of D-allulose;
from 0% to 20% of D-fructose;
from 0% to 10% of glucose;
from 0% to 1.2% of D-allulose dimers.

As indicated above, this preferred permeate can be directly subjected to a concentrating step so as to obtain the stock solution to be crystallized (Stream 7).

It is specified that, in the present application, other than the D-allulose crystals, all of the compositions are generally aqueous compositions. In other words, the solvent of the dry constituents comprises water. The solvent of the compositions generally consists of water or a mixture of water and alcohol such as, for example, ethanol. Preferentially, the solvent of the compositions is water.

Thus, the stock solution of D-allulose of use in the invention generally consists of an aqueous solution of D-allulose The stock solution generally has a dry matter content of at least 75%, for example from 80% to 95%, preferentially from 81% to 92%, most preferentially from 83% to 89%.

In order to achieve this dry matter content, it is necessary to carry out a concentrating step. This step can be carried out on a composition rich in D-allulose, the only requirement is that this composition rich in D-allulose has been obtained by means of a process comprising, in a prior step, the nanofiltration step of use in the invention. This composition rich in D-allulose subjected to the concentrating step can thus be the preferred permeate previously described, but also a composition rich in D-allulose obtained by chromatography, or else a mixture of a permeate with an additional composition rich in D-allulose. Preferentially, the composition rich in D-allulose subjected to the concentrating step is the preferred permeate.

Since the formation of D-allulose dimers also occurs during the concentrating step, it is preferable to select conditions which make it possible to limit the formed amounts of these dimers. The concentrating step is thus generally carried out under vacuum, for example at a pressure of from 5 to 100 mbar, preferably ranging from 20 to 70 mbar. This vacuum makes it possible to decrease the temperature required for the evaporation and to reduce the duration of this concentrating step. It can be carried out at a temperature ranging from 30 to 80° C., advantageously from 34 to 70° C., preferentially from 37 to 50° C. This concentrating step can be carried out in a single-stage evaporator, a multi-stage evaporator, for example a double-stage evaporator. At the end of the concentrating step, the stock solution of D-allulose of use in the invention is obtained.

This concentrating step can be carried out continuously. The stock solution obtained can comprise, by dry mass:
from 80% to 99% of D-allulose, preferably from 85% to 98%;
from 0% to 20% of D-fructose, preferably from 0.5% to 15%;
from 0% to 10% of glucose, preferably from 0% to 5%;
from 0% to 1.5% of D-allulose dimers, for example from 0.1% to 1.2%, preferentially from 0.4% to 1.1%.

The process according to the invention also comprises a step of crystallizing said stock solution of D-allulose so as to form a suspension of D-allulose crystals. This suspension comprises crystals and mother liquors from crystallization which are also formed during this step.

This crystallizing step may be of any type. It may in particular be a crystallizing step by cooling or a crystallizing step by evaporative crystallization. Those skilled in the art will know how to find the implementing conditions which are in particular described in document WO 2011/119004.

However, it should be noted that the crystallizing steps described in these documents are made more difficult to perform because of the particular preparation of the stock solution of use in the invention.

At the end of the crystallizing step, using the suspension of crystals (Stream 9), the crystals (Stream 10) are separated from the mother liquors (Stream 13), in particular by means of a filtering and/or centrifuging step. This separating step is more preferentially carried out batchwise.

The mother liquors (Stream 13) generally have a dry matter content ranging from 70% to 80%.

They can comprise, by dry mass:
from 80% to 99% of D-allulose, preferably from 82% to 95%;
from 0% to 20% of D-fructose, preferably from 0.5% to 15%;
from 0% to 10% of glucose, preferably from 0% to 5%;
from 0% to 3% of D-allulose dimers, for example from 0.1% to 2.9%, in particular from 1% to 2.5%.

The crystals obtained can be subjected to a clarifying step with cold water and/or with alcohol, in particular ethanol. These crystals can then be dried (Stream 11) by means of a drying step which can be carried out in any type of suitable dryer. The D-allulose crystals have a water content of less than 5%, preferably less than 1%.

Figure 5:
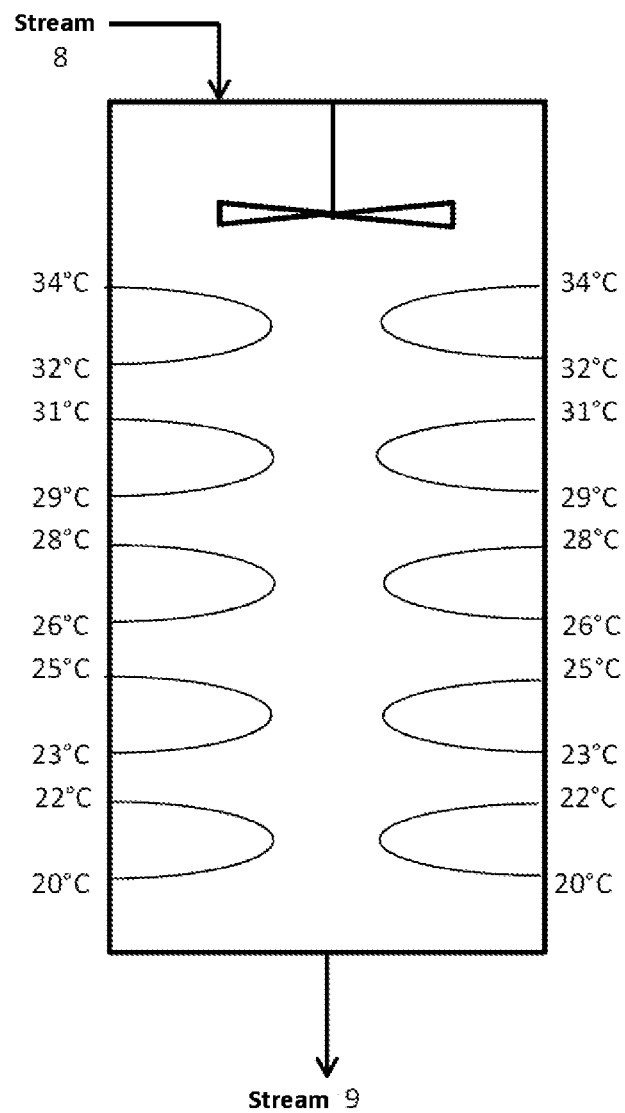
FIG. 5 represents an example of a vertical crystallizer of use in a variant of the process of the invention.

This crystallizing step can be carried out continuously, in particular using a vertical crystallizer, an example of which is represented in FIG. 5.

According to one most preferred mode, the crystallizing step comprises an adiabatic evaporative cooling stage, carried out in an adiabatic crystallizer-evaporator under vacuum so as to form a massecuite (Stream 8), followed by a stage of crystallizing by cooling said massecuite so as to form a suspension of crystals (Stream 9). An adiabatic evaporative cooling causes immediate cooling of the stock solution to be crystallized. Preferably, the crystallizer-evaporator is equipped with a condenser and the water condensed during this stage is continuously reinjected along the walls at the top of the crystallizer so as to keep the dry matter content stable. This preferred crystallizing step comprising two distinct stages, combined with the nanofiltration step in a particular configuration of the process of the invention, has made it possible to continuously obtain the crystals of the invention which are described below in the description. This is linked to the fact that this preferred crystallizing step, in particular the evaporative cooling stage, also makes it possible to very considerably limit the in situ formation of D-allulose dimers. Without being bound to any theory, the applicant explains this by the fact that the stock solution can be cooled virtually instantaneously at the time it is introduced into the crystallizer-evaporator, unlike the already known processes for crystallizing D-allulose which describe the natural cooling of the stock solution, or even by a cooling gradient using a heat exchanger as described in application WO 2016/064087. The crystals according to the invention exhibit an improved purity and improved properties, although the first stage of the crystallizing step is an instantaneous evaporative cooling stage, thereby shortening the duration of the crystallizing step. In point of fact, this is contrary to what would have been envisioned by those skilled in the art, for whom the obtaining of improved crystals requires an increased crystallization time.

During the evaporative cooling stage, the temperature can range from 30 to 40° C., preferably ranging from 33 to 37° C., for example of approximately 35° C. This temperature is easily achieved by those skilled in the art by determining the appropriate reduced pressure to be applied. Thus, the pressure in the crystallizer-evaporator can range from 30 to 50 mbar. An adiabatic crystallizer can in particular be a forced-circulation or indirect forced-circulation (IFC®) DT (for Draft Tube) or DTB (for Draft Tube Baffle) pull tube. Preferably, this evaporative cooling stage is continuous. During this stage, the initiators are continuously generated by a spontaneous nucleation phenomenon in the evaporative crystallizer by the supersaturation created by the rapid cooling: thus, there is, strictly speaking, no introduction of initiators in this case. In a non-limiting manner, a possibility of carrying out this evaporative cooling stage continuously is described in the Examples section and in FIG. 4, wherein a fraction of the crystals formed during the evaporative cooling stage (Stream 7d) is mixed into Stream 7b for feeding the crystallizer-evaporator, thereby making it possible to obtain a Stream 7c which comprises, at the time of the introduction into the crystallizer-evaporator, crystals which will be able to further grow during this new passage through the crystallizer-evaporator. According to this example, Stream 7b can be obtained from a mixture of Stream 7 and of Stream 7a, which consists of a supersaturated syrup of D-allulose recovered in the crystallizer-evaporator, which comprises "fines", that is to say the finest D-allulose crystals of the crystallizer. According to this variant, Stream 7 can advantageously, before mixing, pass through a heat exchanger, said passage making it possible to virtually immediately reheat Stream 7 before immediately mixing it with Stream 7a. This then makes it possible to remelt the fines of Stream 7a and to cool Stream 7 so as to obtain a Stream 7b free of these fines.

At the end of this stage, a massecuite of D-allulose crystals (Stream 8) is recovered, that is to say a suspension of crystals, generally having a small size. The mean residence time of the massecuite during this evaporative cooling stage can be between 5 and 15 hours. The volume mean size D4,3 of the crystals in suspension in the massecuite generally ranges from 50 to 200 μm.

The stage of crystallization by cooling is carried out conventionally by cooling the massecuite obtained during the evaporative cooling stage (Stream 8). The duration of this crystallization stage can range from 25 to 50 hours. The temperature at the start of crystallization generally depends on the temperature of the massecuite introduced and can in particular range from 30 to 40° C., preferably ranging from 33 to 37° C., for example of approximately 35° C. This stage is generally carried with mechanical stirring. Preferably, during the crystallization by cooling, the temperature is decreased at a rate ranging from 0.3 to 0.5° C. per hour. FIG. 5 represents an example of a vertical crystallizer with, on the sides, various heat exchangers making it possible to regulate the temperature in the crystallizer. During this operation, the difference in temperature between the massecuite and the water of the exchanger preferably does not exceed 5° C. The stage of crystallization by cooling can preferably be carried out continuously, in particular in a vertical crystallizer.

Thus, a preferred variant of the process of the invention comprises:
  a step of providing a composition rich in D-allulose (Stream 5);
  a step of nanofiltration of said composition rich in D-allulose so as to provide a retentate (Stream 12) and a permeate (Stream 6);
  a step of recovering the nanofiltration permeate;
  a step of concentrating this permeate so as to provide the stock solution of D-allulose (Stream 7);
  a crystallizing step comprising:
    i. an adiabatic evaporative cooling stage, carried out in an adiabatic crystallizer-evaporator under vacuum so as to form a massecuite (Stream 8),
    ii. followed by a stage of crystallization by cooling of said massecuite so as to form a suspension of crystals (Stream 9).

Other than the advantages associated with the crystals themselves, an advantage of this preferred variant of the process of the invention is that the crystals obtained can be even more easily separated from the mother liquors from crystallization and more easily dried. This is mainly linked to the shape of the crystals obtained.

In order to start up a crystallizing step, D-allulose initiators are generally introduced into the crystallizer selected. These D-allulose initiators consist of D-allulose crystals of small size, having example a size ranging from 10 to 100 μm. The mass amount of initiator can vary widely depending on the type of crystallizer used. It can range from 0.001% to 1%, often from 0.01% to 0.7%, generally from 0.05% to 0.5%, relative to the mass of D-allulose in the stock solution. These amounts are particularly suitable when a step of crystallization by cooling from a stock solution of D-allulose is carried out. As mentioned above, it is also possible to create initiators in situ when an evaporative cooling step is used.

Preferably, the crystallizing step is carried out less than one hour after the concentrating step, preferably less than 30 minutes after said step. Most preferentially, the crystallizing step is carried out immediately after the concentrating step. This makes it possible to further limit, at the time of the crystallizing step, the amount of dimers in the stock solution to be crystallized.

Once recovered after drying, the crystals can also be subjected to an additional sieving step, which makes it possible to screen these crystals and, according to the fraction recovered after sieving, to increase or decrease the size of the crystals. For example, this additional step makes it possible, with respect to the size of the crystals subjected to the sieving step, to recover a fraction with a smaller volume mean size D4,3 of D-allulose crystals passed through the sieve and also a fraction with a larger volume mean size D4,3 of D-allulose crystals remaining in the sieve. In order to modify the crystal population and to obtain the desired D4,3 fraction, it is sufficient for those skilled in the art to select the sieve mesh size.

It goes without saying that the process according to the invention can comprise other steps, such as the other steps which appear in the conventional process previously described and which will subsequently be described in detail. The process according to the invention can also comprise additional purification steps and also intermediate diluting or concentrating steps with a view to regulating the dry matter content and thus to carrying out the various steps of the process of the invention under the best conditions. All of these steps can be carried out continuously.

The composition of D-fructose provided (Stream 1) for carrying out the epimerizing step can be a D-fructose syrup, which can be obtained by dissolving D-fructose crystals in water or a glucose/D-fructose syrup. Preferentially, this composition comprises a glucose/D-fructose syrup which comprises at least 90% by dry weight of D-fructose, preferentially at least 94% of D-fructose. In one preferred mode that will be explained later in the description, the D-fructose composition provided for carrying out the subsequent epimerizing step is a mixture (Stream 1') of this D-fructose syrup with at least one recycled fraction which may be the raffinate as a whole or in part (Stream 14 or 16), it being possible for this recycled fraction to comprise a greater amount of D-allulose.

The D-fructose composition subjected to the epimerizing step can comprise:
from 0% to 10% of D-allulose;
from 70% to 100% of D-fructose;
from 0% to 10% of glucose;
from 0% to 15% of D-allulose dimer.

The epimerizing step is carried out using the D-fructose composition previously provided, optionally after regulation of the dry matter content. This step is generally carried out at a dry matter content ranging from 30% to 60%, often from 45% to 55%. An enzyme of D-psicose epimerse type or a composition comprising this enzyme is introduced into this composition. The composition comprising this enzyme may be a lyophilisate of a host microorganism which synthesizes D-psicose epimerase, said microorganism possibly being *Bacillus subtilis*, in particular the one described in application WO 2015/032761 A1. The pH is regulated according to the enzyme used, for example at a pH ranging from 5.5 to 8.5. The reaction can be carried out by heating at a temperature ranging from 40 to 70° C., often from 45 to 60° C. The reaction can last from 0.1 to 100 hours, for example from 0.2 to 60 hours. This reaction can for example be carried out on an enzymatic column, thereby having the advantage of also working continuously on this step. It is also possible, in order to operate continuously, to work sequentially with several reactors. In order to carry out this epimerizing step, use may particularly be made of the teaching of document WO 2015/032761 A1.

At the end of the reaction, a composition comprising D-fructose and D-allulose, generally according to a D-fructose/D-allulose weight ratio ranging from 85/15 to 55/45, often according to a D-fructose/D-allulose weight ratio ranging from 80/20 to 60/40, is formed. This ratio depends on the epimerization parameters used and, quite obviously, on the amount of D-allulose and of D-fructose in the D-fructose composition provided in the epimerizing step; the amount of D-allulose in this composition may in particular be greater in the case of recycling.

At the end of this epimerizing step, if necessary, a filtration step can be carried out in order to recover the cell debris possibly present, in particular when a lyophilisate of a host microorganism is used. This step may consist of a microfiltration step. In FIG. 3, the microfiltered composition corresponds to Stream 3 and the cell debris is recovered in Stream 17.

In the process of the invention, additional purifying steps can also be carried out. Generally carried out, before the chromatography step, is a step of demineralizing the composition comprising D-fructose and D-allulose (Stream 3), which can be carried out by passing it through one or more cationic ion exchange resins (for example a cationic resin of Dowex 88 type), anionic ion exchange resins (for example an anionic resin of Dowex 66 type) and a cationic-anionic mixture. In FIG. 3, this composition corresponds to Stream 4. The composition comprising D-fructose and D-allulose obtained is then demineralized and generally has a resistivity greater than 100 kΩ·cm$^{-1}$. It is also possible to carry out, before this demineralizing step, a step of decoloring the composition comprising D-fructose and D-allulose, for example by passing it over a column comprising active carbon.

The composition comprising D-fructose and D-allulose (Stream 4) can then be subjected to a chromatography step in order to provide at least one composition rich in D-allulose and one composition rich in D-fructose. In one preferred mode that will be explained in detail later in the description, the composition comprising D-fructose and D-allulose, which is subjected to the chromatography step, is a mixture (Stream 4') of the composition resulting from the epimerizing step (Stream 4) and of at least one recycled fraction, this recycled fraction possibly comprising a greater amount of D-allulose.

The composition subjected to the chromatography step can comprise, relative to its dry mass:
from 22% to 45% of D-allulose, generally from 25% to 37%;
from 45% to 75% of D-fructose, generally from 46% to 70%;
from 0% to 10% of glucose;
from 2% to 10% of D-allulose dimer.

In order to carry out this chromatography step, it is possible to use any type of continuous chromatography, in particular of Simulated Moving Bed (SMB) type, of Improved Simulated Moving Bed (ISMB) type, of Divide Improved Simulated Moving Bed (DISMB) type, of Sequential Simulated Moving Bed (SSMB) type or of Nippon Mitsubishi Chromatography Improved (NMCI) type. Water is generally used as eluent. The chromatograph can be equipped with several columns in series, for example from 4 to 8 columns. The columns comprise ion exchange resin, for example a cationic resin for exchanging calcium ions. The dry matter content of the composition comprising D-fructose and D-allulose can range from 40% to 70%, and is generally approximately 50%. The temperature of the composition during the chromatography generally ranges from 40 to 80° C., preferably from 55 to 65° C. This chromatography lasts for the amount of time required to obtain satisfactory separation and can last for several hours.

At the end of this step, a composition which in D-allulose (Stream 5) which can comprise, relative to its dry matter content, at least 80% of D-allulose, advantageously at least 90% of D-allulose, is obtained. This composition rich in D-allulose can have a dry matter content ranging from 5% to 15%. At the end of this step, a raffinate (Stream 14), which generally comprises, relative to its dry matter content, at least 75% of D-fructose, often at least 80% of D-fructose, is also obtained. This raffinate generally has a dry matter content ranging from 15% to 30% approximately.

The composition rich in D-allulose obtained at the end of the chromatography (Stream 5), thus can comprise, relative to its dry mass:
from 80% to 98% of D-allulose;
from 0% to 20% of D-fructose;
from 0% to 10% of glucose;
from 1.5% to 5% of D-allulose dimer.

The raffinate can comprise, for its part, relative to its dry mass:
from 1% to 10% of D-allulose;
from 70% to 99% of D-fructose;
from 0% to 10% of glucose;
from 5% to 20% of D-allulose dimer.

Contrary to a conventional process wherein, relative to the D-fructose introduced, the overall yield of D-allulose crystals is less than 15%, the yield of the process of the invention can be greater than or equal to 25%. Advantageously, the overall yield of D-allulose crystals is greater than or equal to 50%, for example greater than or equal to 60%, or even greater than or equal to 65%. This particularly improved yield is made possible by the fact that it is possible to perform recycling steps without disrupting the crystallizing step.

Thus, the process of the invention can comprise at least one recycling step.

According to one preferred mode, this recycling step can consist of a step of recycling at least one part of the raffinate resulting from the chromatography step (Stream 14). This raffinate can optionally have been concentrated before being mixed. It can advantageously be totally or partly recycled, so as to be mixed with D-fructose (Stream 1), for example in the form of the D-fructose/glucose syrup previously described, in order to provide the D-fructose composition (Stream 1'). It is then this D-fructose composition, which is generally richer in D-allulose than the D-fructose syrup, which is subjected to the epimerizing step.

This recycling step can consist of a step of recycling at least one part of the mother liquors (Stream 13). These mother liquors can advantageously be totally or partly recycled, so as to be mixed with the composition comprising D-fructose and D-allulose (Stream 4). It is then this mixture (Stream 4') which is subjected to the chromatography step. These mother liquors may optionally have been diluted before being mixed.

This recycling step can consist of a step of recycling at least one part of the retentate (Stream 12). This retentate can advantageously be totally or partly recycled, so as to be mixed with the composition comprising D-fructose and D-allulose (Stream 4) and optionally the recycled mother liquors. It is then this mixture (Stream 4') which is subjected to the chromatography step. This retentate can optionally have been concentrated before being mixed. In the case where the mixing is carried out with the retentate and mother liquor fractions, it may not be necessary to concentrate or dilute these fractions. It should be noted that the recyclings of the retentate and mother liquor fractions, which are two fractions having relatively large amounts of D-allulose, make it possible to increase the richness in D-allulose (and consequently to decrease the amount of D-fructose) of the composition subjected to the chromatography step.

In order to carry out the optional steps of concentrating the recycled fractions, it is possible to use the same equipment and conditions described for the concentrating step allowing the production of the stock solution.

According to one most preferred mode of the invention (FIG. 3 represents a circuit for production with this preferred process of the invention), the process comprises:
a) a step of providing a composition comprising D-fructose (Stream 1');
b) an epimerizing step so as to form a composition comprising D-fructose and D-allulose (Stream 2);
c) a chromatography step so as to provide a composition rich in D-allulose (Stream 5) and a raffinate consisting of a composition rich in D-fructose (Stream 14);
d) a step of nanofiltration of the composition rich in D-allulose so as to provide a permeate (Stream 6) and a retentate (Stream 12);
e) a step of concentrating the permeate so as to form the stock solution to be crystallized (Stream 7);
f) a step of crystallizing the stock solution (Stream 9) so as to form crystals (Stream 10) and mother liquors (Stream 13);

and in said process are carried out:
a step of recycling at least one part of the raffinate (Stream 14 or 16) so as to be mixed with D-fructose (Stream 1) and provide the composition (Stream 1') of step a);
and/or a step of recycling at least one part of the retentate (Stream 12) resulting from the nanofiltration step so as to be mixed with the composition comprising D-fructose and D-allulose (Stream 4) resulting from step b) so as to provide the composition (Stream 4') subjected to the chromatography step c);
and/or a step of recycling at least one part of the mother liquors (Stream 13) resulting from the crystallizing step so as to be mixed with the composition comprising D-fructose and D-allulose resulting from step b) (Stream 4) so as to provide the composition (Stream 4') subjected to the chromatography step c).

The process comprises a flushing step, this flushing step possibly being a step of flushing at least one part of at least one of the recycled fractions chosen from the raffinate, the retentate and the mother liquors from crystallization. This is because, in order for the system to remain stable, it is absolutely necessary to remove from the production circuit a part of the D-allulose dimers formed during the process. Generally, the more the fractions are recycled, the more the amount of D-allulose dimers increases in the circuit. Thus, one possibility for decreasing the amount of D-allulose dimers is to increase the amounts flushed. However, this then occurs to the detriment of the overall yield of D-allulose crystals. The process of the invention makes it possible to drastically increase the recycling of the various fractions obtained in the process, while at the same time keeping crystallization possible.

By way of example, in the variant of the most preferred process described above, wherein all the raffinate, retentate and mother liquor from crystallization fractions are recycled, the raffinate recycling step is advantageously a partial recycling, for example from 50% to 95% of this raffinate is recycled (Stream 16) and from 5% to 50% is flushed (Stream 15), so as to provide a D-fructose composition which comprises D-allulose dimers; in other words, the degree of recycling of the composition rich in D-fructose ranges from 50% to 95%. Preferentially, the degree of recycling ranges from 70% to 92%. In this case, the other two recyclings are advantageously total recyclings.

The fractions flushed can then be used to produce syrups, optionally after a step of concentrating and/or of mixing with other compositions and/or additives.

Because the crystallizing step remains stable over time, the process according to the invention is particularly advantageous since it can be continuous.

As previously explained, according to the preferred variant of the invention combining the step of nanofiltration and crystallization in an adiabatic crystallizer-evaporator under vacuum, the applicant has also succeeded in obtaining crystals with an improved quality.

The crystals according to the invention have a mass content of D-allulose dimer of less than 0.50%, preferably less than 0.30%, or even less than 0.20%. These crystals can advantageously comprise a mass content of D-allulose dimer ranging from 0.01% to 0.48%, preferentially ranging from 0.02% to 0.45%, for example ranging from 0.03% to 0.40%, in particular from 0.04% to 0.30%, particularly from 0.05% to 0.20%.

The crystals according to the invention advantageously have a mass content of D-allulose of greater than or equal to 99.00%, preferably greater than or equal to 99.50%, or even greater than or equal to 99.70% One advantage of the crystals of the invention is that these crystals exhibit small amounts of D-allulose dimer. Without being bound by any theory, the applicant explains this by the fact that the stock solution of use for the production of these crystals comprises a very small D-allulose dimer content and by the fact that the crystallizing step carried out makes it possible to limit the formation of these dimers in situ. It has thus been possible for the applicant to obtain these crystals by means of this process by combining the nanofiltration step with the crystallizing step comprising a stage of adiabatic evaporative cooling and a stage of crystallization by cooling.

One disadvantage associated with the prior art D-allulose crystals, which comprise a higher dimer content than those of the invention, is that an elongation of these crystals so as to have a shape similar to needles is observed, in particular when they are large.

Preferentially, the D-allulose crystals of the invention have a volume mean size D4,3 of greater than 200 µm, advantageously ranging from 210 to 800 µm, preferentially from 220 to 350 µm.

Figure 11:
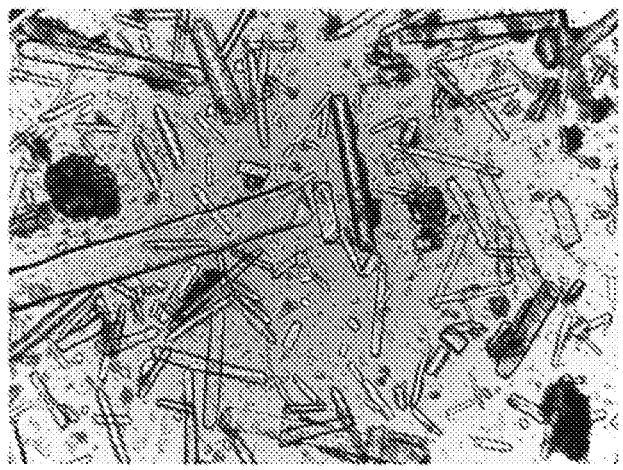
FIG. 11 represents an image obtained by optical microscopy of comparative D-allulose crystals.
Figure 12:
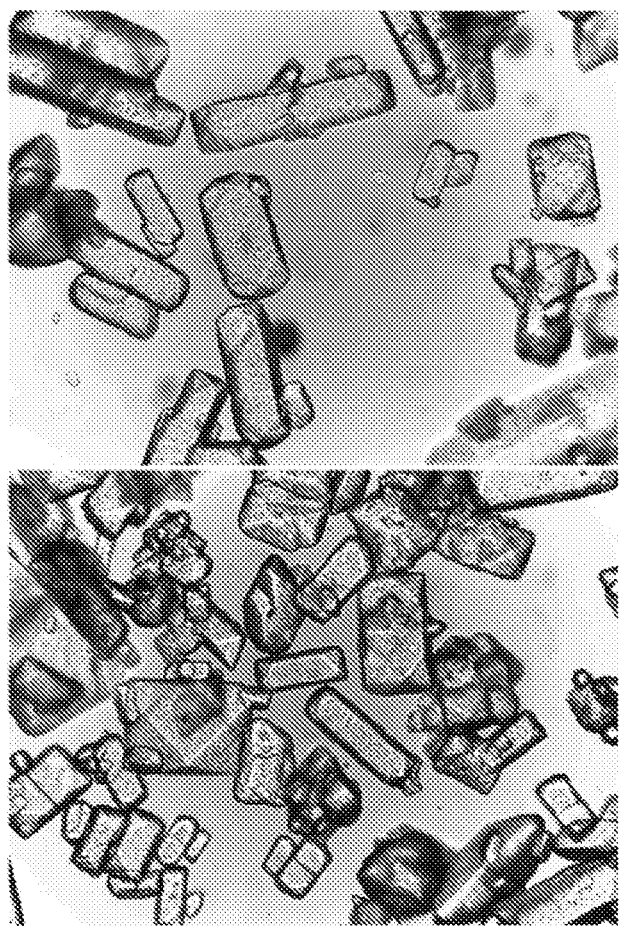
FIG. 12 represents two images obtained by optical microscopy of D-allulose crystals according to the invention.
Figure 13:
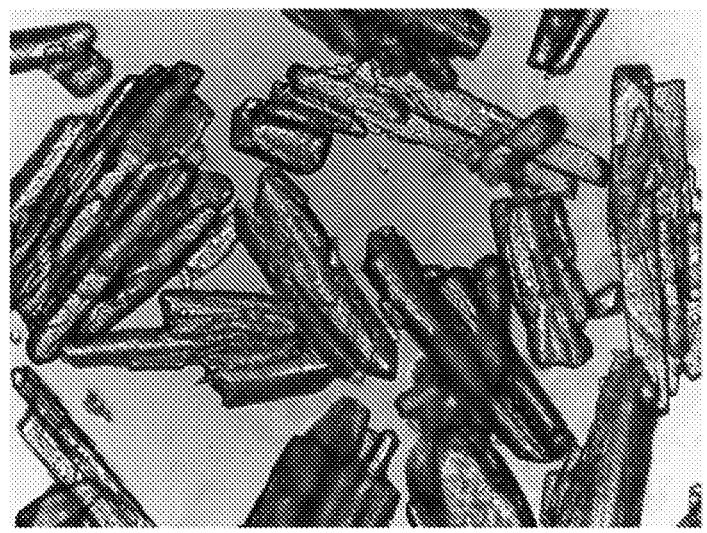
FIG. 13 represents an image obtained by optical microscopy of D-allulose crystals produced and sold by the company CJ CheilJedang Food Ingredient.

The crystals of the invention, which have a lower D-allulose dimer content, have the advantage of having a more "squat" shape, as demonstrated in FIGS. 11, 12 and 13.

Figure 15:
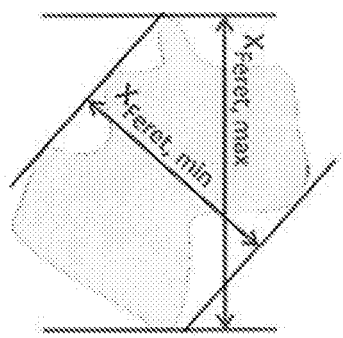
FIG. 15 represents the diameters Feret min and Feret max of a model particle.

This more squat shape can result in the fact that the D-allulose crystals of the invention can have, for a given volume particle size D4,3 chosen in the range of from 200 to 400 µm, a Feret min/Feret max ratio greater than 0.60, advantageously ranging from 0.62 to 0.90, for example from 0.63 to 0.80. The Feret diameter is a parameter well known to those skilled in the art. It is deduced from the projected area of a particle, using the principle of the caliper. The Feret min diameter consists of the smallest of the dimensions, whereas the Feret max diameter consists of the largest of the dimensions. FIG. 15 represents the principle of the Feret min and max diameters on a given particle.

Preferably, the crystals of the invention exhibit this Feret min/Feret max ratio over all of the particle sizes in the range of from 200 to 400 µm.

Alternatively and independently of the content of D-allulose dimers, a subject of the invention relates to D-allulose crystals which have a volume mean size D4,3 of greater than 200 µm, advantageously ranging from 210 to 800 µm, preferentially from 220 to 350 µm and which have, for a given volume particle size D4,3 chosen from the range extending from 200 to 400 µm, a Feret min/Feret max diameter ratio of greater than 0.60, advantageously ranging from 0.62 to 0.90, for example from 0.63 to 0.80. Preferably, the crystals of the invention have this Feret min/Feret max ratio over all of the particle sizes in the range extending from 200 to 400 µm.

These crystals of the invention advantageously comprise a mass content of D-allulose dimer of less than 0.50%, preferably less than 0.30%, or even less than 0.20%. These crystals may advantageously comprise a mass content of D-allulose dimer ranging from 0.01% to 0.48%, preferentially ranging from 0.02% to 0.45%, for example ranging from 0.03% to 0.40%, in particular from 0.04% to 0.30%, particularly from 0.05% to 0.20%. These crystals advantageously have a mass content of D-allulose of greater than or equal to 99.00%, preferably greater than or equal to 99.50%, or even greater than or equal to 99.70%.

The volume mean size D4,3 and also the Feret min/Feret max diameter ratio of the crystals are determined using a particle size analyzer, in particular the particle size analyzer of QICPIC RODOS type of the brand SympaTEC such as that used in the Examples section. Given that the crystals are observed randomly in all directions in a particle size analyzer, the values obtained by a particle size analyzer for a population of crystals are different from the values obtained by calculation on a single microscopic image of this population of crystals, the values obtained by particle size analysis generally being higher.

Preferably, the crystals are non-agglomerated (or individualized). The fact that the crystals are non-agglomerated can be verified by simple observation by optical microscopy. By way of example, the crystals of FIG. 13 are agglomerated, unlike those of FIGS. 11 and 12.

This different form results, on the macroscopic scale, in an improved flow of the crystals of the invention in comparison with crystals of the same mean size. Likewise, these crystals can exhibit better behavior with respect to caking over time.

Thus, because of their properties, the crystals obtained by means of the preferred process of the invention can flow easily. They have thus made it possible to obtain crystals exhibiting a flow never achieved to date. They can thus be, for example, advantageously used as table sugar.

The D-allulose crystals of the invention can be used in the known applications of allulose and, generally, sweeteners. Among the applications that can use the D-allulose crystals of the invention, mention may be made of chewing gums in the form of sticks or dragees, candies and tablets to be sucked, biscuits, cookies, muffins, cakes, gelatin-based cakes, chewing pastes, in particular chewing pastes with a short texture, icings and powdered drinks.

Another subject of the invention also relates to the use of a nanofiltration unit in a circuit for producing D-allulose crystals in order to improve the stability of the process and/or the overall yield of D-allulose crystals. This use is particularly advantageous when the raw material introduced into the circuit comprises D-fructose.

Another subject of the invention also relates to the use of a nanofiltration unit in a circuit for producing D-allulose crystals for improving the quality of the crystals obtained. The term "improving the quality of the crystals obtained" is intended to mean in particular reducing the D-allulose dimer content and/or increasing the Feret min/Feret max diameter ratio of the D-allulose crystals.

By way of illustration, other embodiments of the process according to the invention, comprising a mother liquor recycling step and/or a raffinate recycling step and/or a retentate recycling step are presented below.

According to a first embodiment, the process comprises:
a) a step of providing a composition rich in D-allulose;
b) a concentrating step so as to form the stock solution to be crystallized;

characterized in that:
at least one recycling step consists of a step of recycling at least one part of the mother liquors;
the nanofiltration step is carried out on these recycled mother liquors so as to form a permeate and a retentate;
the permeate is mixed with the composition rich in D-allulose provided in step a); and
this mixture is subjected to the concentrating step b) so as to provide the stock solution to be crystallized;
at least one part of the mother liquors and/or of the retentate is flushed.

According to a second embodiment, the process comprises:
a) a step of providing a composition rich in D-allulose;
b) a concentrating step so as to form the stock solution to be crystallized;
characterized in that:
at least one recycling step consists of a step of recycling at least one part of the mother liquors;
these recycled mother liquors are mixed with the composition rich in D-allulose provided in step a);
the nanofiltration step is carried out on this mixture so as to provide a permeate and a retentate;
this permeate is subjected to the concentrating step b) so as to provide the stock solution to be crystallized; and
at least one part of the mother liquors is flushed.

According to a third embodiment, the process comprises:
a) a step of providing a composition comprising D-allulose and D-fructose;
b) a chromatography step so as to provide a composition rich in D-allulose and a raffinate consisting of a composition rich in D-fructose;
c) a step of concentrating the composition rich in D-allulose so as to form the stock solution to be crystallized;
characterized in that:
at least one recycling step consists of a step of recycling at least one part of the mother liquors;
the nanofiltration step is carried out on these recycled mother liquors so as to form a permeate and a retentate;
the permeate is mixed with the composition provided in step a);
this mixture is subjected to the chromatography step b); and
at least one part of the mother liquors is flushed.

According to a fourth embodiment, the process comprises:
a) a step of providing a composition comprising D-allulose and D-fructose;
b) a chromatography step so as to provide a composition rich in D-allulose and a composition rich in D-fructose;
c) a concentrating step so as to form the stock solution to be crystallized;
characterized in that:
at least one recycling step consists of a step of recycling at least one part of the mother liquors;
these recycled mother liquors are mixed with the composition provided in step a);
the nanofiltration step is carried out on this mixture so as to provide a permeate and a retentate;
this permeate is subjected to the chromatography step b); and
at least one part of the mother liquors is flushed.

According to a fifth embodiment, the process comprises:
a) a step of providing a composition comprising D-allulose and D-fructose;
b) a chromatography step so as to provide a composition rich in D-allulose and a composition rich in D-fructose;
c) a concentrating step so as to form the stock solution to be crystallized;
characterized in that:
at least one recycling step consists of a step of recycling at least one part of the mother liquors;
these recycled mother liquors are mixed with the composition provided in step a);
the chromatography step b) is carried out on this mixture;
the nanofiltration step is carried out on the composition rich in D-allulose resulting from this chromatography step b), so as to provide a permeate and a retentate;
this permeate is subjected to the concentrating step c); and
at least one part of the mother liquors is flushed.

According to a sixth embodiment, the process comprises:
a) a step of providing a composition comprising D-fructose;
b) an epimerizing step so as to form a composition comprising D-fructose and D-allulose;
c) a step of chromatography of this composition so as to provide a composition rich in D-allulose and a raffinate consisting of a composition rich in D-fructose;
d) a step of concentrating the composition rich in D-allulose so as to form the stock solution to be crystallized;
characterized in that:
at least one recycling step consists of a step of recycling the raffinate;
the nanofiltration step is carried out on this raffinate so as to provide a permeate and a retentate;
the permeate is mixed with the composition comprising D-fructose of step a);
the epimerizing step b) is carried out on this mixture; and
at least one part of the raffinate is flushed.

According to a seventh embodiment, the process comprises:
a) a step of providing a composition comprising D-fructose;
b) an epimerizing step so as to form a composition comprising D-fructose and D-allulose;
c) a step of chromatography of this composition so as to provide a composition rich in D-allulose and a raffinate consisting of a composition rich in D-fructose;
d) a concentrating step so as to form the stock solution to be crystallized;
characterized in that:
a recycling step consists of a step of recycling the raffinate obtained in step c);
a first nanofiltration step is carried out on this raffinate so as to provide a first permeate and a first retentate;
the first permeate is mixed with the composition comprising D-fructose of step a);
the epimerizing step b) is carried out on this mixture;
a recycling step consists of a step of recycling at least one part of the mother liquors;
a second nanofiltration step is carried out on these recycled mother liquors so as to form a second permeate and a second retentate;
the second permeate is mixed with the composition rich in D-allulose provided in step c);
this mixture is subjected to the concentrating step d) so as to provide the stock solution to be crystallized; and
at least one part of the raffinate and/or of the mother liquors is flushed.

According to an eighth embodiment, the process comprises:
a) a step of providing a composition comprising D-fructose;
b) an epimerizing step so as to form a composition comprising D-fructose and D-allulose;
c) a step of chromatography of this composition so as to provide a composition rich in D-allulose and a raffinate consisting of a composition rich in D-fructose;
d) a concentrating step so as to form the stock solution to be crystallized;
characterized in that:
a recycling step consists of a step of recycling the raffinate obtained in step c);
a first nanofiltration step is carried out on this raffinate so as to provide a first permeate and a first retentate;

the first permeate is mixed with the composition comprising D-fructose of step a);
the epimerizing step b) is carried out on this mixture;
a recycling step consists of a step of recycling at least one part of the mother liquors;
these recycled mother liquors are mixed with the composition rich in D-allulose provided in step c);
a second nanofiltration step is carried out on this mixture so as to provide a second permeate and a second retentate;
this second permeate is subjected to the concentrating step d) so as to provide the stock solution to be crystallized; and
at least one part of the raffinate and/or of the mother liquors is flushed.

According to a ninth embodiment, the process comprises:
a) a step of providing a composition comprising D-fructose;
b) an epimerizing step so as to form a composition comprising D-fructose and D-allulose;
c) a chromatography step so as to provide a composition rich in D-allulose and a raffinate consisting of a composition rich in D-fructose;
d) a step of concentrating the composition rich in D-allulose so as to form the stock solution to be crystallized;
characterized in that:
a recycling step consists of a step of recycling the raffinate obtained in step c);
a first nanofiltration step is carried out on this raffinate so as to provide a first permeate and a first retentate;
the first permeate is mixed with the composition comprising D-fructose of step a);
the epimerizing step b) is carried out on this mixture;
a recycling step consists of a step of recycling at least one part of the mother liquors;
a second nanofiltration step is carried out on these recycled mother liquors so as to form a second permeate and a second retentate;
the second permeate is mixed with the composition formed in step b);
this mixture is subjected to the chromatography step c); and
at least one part of the raffinate and/or of the mother liquors is flushed.

According to a tenth embodiment, the process comprises:
a) a step of providing a composition comprising D-fructose;
b) an epimerizing step so as to form a composition comprising D-fructose and D-allulose;
c) a chromatography step so as to provide a composition rich in D-allulose and a raffinate consisting of a composition rich in D-fructose;
d) a step of concentrating the composition rich in D-allulose so as to form the stock solution to be crystallized;
characterized in that:
a recycling step consists of a step of recycling the raffinate obtained in step c);
a first nanofiltration step is carried out on this raffinate so as to provide a first permeate and a first retentate;
the first permeate is mixed with the composition comprising D-fructose of step a);
the epimerizing step b) is carried out on this mixture;
a recycling step consists of a step of recycling at least one part of the mother liquors;
these recycled mother liquors are mixed with the composition formed in step b);
a second nanofiltration step is carried out on this mixture so as to provide a second permeate and a second retentate;
this second permeate is subjected to the chromatography step c); and
at least one part of the raffinate and/or of the mother liquors is flushed.

According to an eleventh embodiment, the process comprises:
a) a step of providing a composition comprising D-fructose;
b) an epimerizing step so as to form a composition comprising D-fructose and D-allulose;
c) a chromatography step so as to provide a composition rich in D-allulose and a raffinate consisting of a composition rich in D-fructose;
d) a step of concentrating the composition rich in D-allulose so as to form the stock solution to be crystallized;
characterized in that:
a recycling step consists of a step of recycling the raffinate obtained in step c);
a first nanofiltration step is carried out on this raffinate so as to provide a first permeate and a first retentate;
the first permeate is mixed with the composition comprising D-fructose of step a);
the epimerizing step b) is carried out on this mixture;
a recycling step consists of a step of recycling at least one part of the mother liquors;
these recycled mother liquors are mixed with the composition formed in step b);
the chromatography step c) is carried out on this mixture;
a second nanofiltration step is carried out on the composition rich in D-allulose resulting from this chromatography step b), so as to provide a second permeate and a second retentate;
this second permeate is subjected to the concentrating step c); and
at least one part of the raffinate and/or of the mother liquors is flushed.

In a non-limiting manner, the invention will now be explained in detail with a view to illustrating the advantages thereof, in the examples below.

EXAMPLES

Analytical Methods
Gas Chromatography
The gas chromatograph used is of Varian 3800 type and is equipped with:
A split-splitless injector (with or without dividers);
A flame ionization detector (FID);
A computer system for processing the signal from the detector;
An automatic sampler (type 8400).

The various amounts are determined by gas chromatography in the form of methoximated trimethylsilyl derivatives, then quantified by the internal calibration method.

Determination of the D-Allulose, D-Fructose and Glucose Contents

The response coefficients applied are 1.25 for D-allulose and D-fructose and 1.23 for glucose.

The other monosaccharides were not detected.

Preparation of the Sample

In a dish for taring, weigh out 100 to 300 mg of the sample to be tested+10 ml of internal standard solution consisting of methyl α-D-glucopyranoside at 0.3 mg/ml in pyridine. Remove 0.5 ml from the dish for taring and place in a 2 ml pot and evaporate to dryness under a nitrogen stream. Add 20 mg of methoxylamine hydrochloride and 1 ml of pyridine. Stopper and leave in the Reacti-therm® incubation system at 70° C. for 40 min. Add 0.5 ml of N,O-Bis (trimethylsilyl)trifluoroacetamide (BSTFA). Heat for 30 min at 70° C.

Chromatographic Conditions
Column: DB1 capillary 40 meters, internal diameter of 0.18 mm, film thickness 0.4 µm, 100% constituted of dimethylpolysiloxane, non-polar (J&W Scientific ref.: 121-1043)
Column temperature: 100° C. programming up to 260° C. at a rate of 3° C./min, then up to 300° C. at 15° C./min, maintain for 5 min at 300° C.
Injector temperature: 300° C.
Detector temperature: 300° C. (Range $10^{-12}$)
Pressure: 40 psi (constant flow rate)
Vector gas: Helium
Injection mode: Split (Split flow rate: 100 ml/min)
Injected volume: 1.0 µl D-allulose, D-fructose and glucose were detected in this order. D-allulose, which was unknown, has a retention time under these conditions of between 39.5 and 40 minutes.

Determination of the Contents of D-Allulose Dimers and Glucose-Glucose Dimers

The response coefficients applied are 1.15 for the D-allulose dimers and maltose, and 1.08 for isomaltose. The other glucose dimers were not detected.

Preparation of the Sample:
In a dish for taring, weigh out 100 to 300 mg of the sample to be tested+10 ml of internal standard solution consisting of Phenyl beta-D-glucopyranoside at 0.3 mg/ml in pyridine.

Remove 0.5 ml from the dish for taring and place in a 2 ml pot and evaporate to dryness under a nitrogen stream.

Take up with 0.5 ml of the solution of hydroxylamine hydrochloride at 40 g/l in pyridine, stopper, stir and leave at 70° C. for 40 min.

Add 0.4 ml of BSTFA and 0.1 ml of N-Trimethylsilylimidazole (TSIM). Heat for 30 min at 70° C.

Chromatographic Conditions
Column: DB1 capillary 30 meters, internal diameter of 0.32 mm, film thickness 0.25 µm (J&W Scientific ref.: 123-1032)
Column temperature: 200° C. programming up to 280° C. at a rate of 5° C./min (maintain for 6 min), then up to 320° C. at 5° C./min, maintain for 5 min at 320° C.
Injector temperature: 300° C.
Detector temperature: 300° C. (Range $10^{-12}$)
Pressure: 14 psi (constant flow rate)
Vector gas: Helium
Injection mode: Split (Split flow rate: 80 ml/min)
Injected volume: 1.2 µl Expression of the Results:
The content of the various constituents is expressed in g per 100 g of crude product and is given by the following equation:

$$\% \text{ constituent } i = \frac{Si}{Se} \times \frac{Pe}{P} \times \frac{100}{Ki}$$

With:
Si=surface area of the peak(s) of constituent i
Se=surface area of the internal standard peak
Pe=weight of internal standard introduced into the beaker (in mg)
P=weight of standard weighed out (in mg)
Ki=response coefficient of the constituent i If the percentage obtained (expressed herein on a crude basis) exceeds 20% for one of the constituents, the sample is diluted and the GC analysis recommenced in order to obtain a mass amount of less than 20%.

The mass amounts expressed on a crude basis are then expressed on a dry basis, by dividing for the dry matter content of the sample tested.

The mass amounts of D-allulose, of D-fructose and of glucose are easily determined, since none of the characteristic peaks are co-eluted.

The peak of the maltose and of the D-allulose dimers may be co-eluted. However, it should be noted that, in the crystals of the invention and described in the examples below, maltose is never present.

If the characteristic peaks of maltose are not detected, the surface area Si of the D-allulose dimers is determined by integration of the unknown peaks, between 10 and 17 minutes. If the characteristic peaks of maltose are detected (which may be the case in the syrups of the invention), the amounts of maltose are determined and this amount is subtracted from the total amount of the dimers.

In order to determine the total amount of glucose-glucose dimers, the following protocol is carried out on a sample:
Hydrochloric hydrolysis
In a 15 ml hydrolysis tube with a screw cap made of Teflon, weigh out about precisely from 50 to 500 mg of sample (adjust the weighing out according to the expected sugar content), add 2 ml, with a two graduation mark pipette, of the internal standard solution (galactitol at 5 mg/ml in osmosed water), add 3 ml of water and 5 ml of the 4N HCl solution.
Stopper hermetically, stir for 1 min with a vortex stirrer. Place the tube in a thermostatted dry bath regulated at 100° C. for 1 hour, stirring with a vortex from time to time.
Demineralization and concentration
After cooling, deposit the entire hydrolysis in a 50 ml beaker. Add 6 to 8 g of a 50/50 mixture of AG4 X 4 and AG50 W 8 anionic resin. Leave to stir magnetically for 5 minutes. Filter on paper. Recover the liquor and repeat the demineralization step until a pH close to water is obtained.
Preparation of the sample
In a dish for taring, weigh out 100 to 300 mg of the sample to be tested+10 ml of internal standard solution consisting of methyl α-D-glucopyranoside at 0.3 mg/ml in pyridine. Remove 0.5 ml from the dish for taring and place in a 2 ml pot and evaporate to dryness under a nitrogen stream. Add 20 mg of methoxylamine hydrochloride and 1 ml of pyridine. Stopper and leave in the Reacti-therm® at 70° C. for 40 min. Add 0.5 ml of BSTFA. Heat for 30 min at 70° C.

The amount of total glucose of the solution (which comprises the initial glucose termed "free" and the glucose resulting from the hydrolysis and in particular linked to the presence of maltose and isomaltose) is determined by GC analysis of the glucose. The amount of maltose and, by the difference between the total amount of dimers attributed to the peaks between 10 and 17 minutes, the amount of D-allulose dimers are easily deduced therefrom.

Particle Size Analysis
The volume mean size D4,3 values and also the ratio of Feret min/Feret max diameters of the crystals are determined on a particle size analyzer of QICPIC RODOS type of the brand SympaTEC, equipped with its powder (dry process) dispersion module, by following the technical manual and the specifications of the manufacturer.

Implementation of Continuous Industrial Processes for Producing D-Allulose Crystals

Example 1

Example 1 consists of a method for continuous production of D-allulose crystals. The steps of the process used are described in detail in FIG. 3. The composition and the flow rate of the Streams after stabilization in the process are described in Tables 1a and 1 b.

Step 1:

13.1 metric tons of a mixture composed of 26% of a Fructamyl D-fructose syrup (Tereos) comprising 95% of D-fructose at 50% dry matter content (DM) (Stream 1), and 74% of Stream 16 brought to 50% DM, are introduced into a stirred batch reactor with a working volume of 12 m³. The whole mixture (Stream 1') is maintained at 55° C. A lyophilisate of the *Bacillus subtilis* host strain of the D-psicose 3 epimerase enzyme detailed in patent WO 2015/032761 is introduced into the tank in sufficient amount to have $2.5 \times 10^7$ units of activity in the reactor. Five reactors are used sequentially so as to provide a syrup composed essentially of fructose and allulose (Stream 2) continuously at a flow rate of 1.3 t/h. The reaction conditions are the following:

Temperature: 55° C.
pH=7
Reaction time 48 h

At the end of the reaction, the Stream 2 obtained comprises a richness in D-allulose approximately equal to 25% and a richness in D-fructose approximately equal to 75%.

Step 2:

Stream 2 passes through a microfiltration membrane during a batchwise operation. A Stream 3 free of cell debris is obtained, along with a microfiltration retentate (Stream 17) comprising the debris resulting from the *Bacillus subtilis* lyophilisate, which is flushed from the circuit. The microfiltration parameters are as follows:

Transmembrane pressure: 0-3 bar
Pore size: 0.1 μm
Temperature: 50° C.
Mean flow rate: 15 l/h/m²
Membrane: Sepro PS35
Volume Concentration Factor: 33

TABLE 1a

Flow rates and composition of the Streams of steps 1 to 5 of Example 1

| Step/Characteristics of the Streams | Stream | | |
|---|---|---|---|
| Step 1 | Stream 1 | Stream 16 | Stream 1' |
| Flow rate by mass (kg/h) | 360 | 1005 | 1365 |
| Dry Matter (%) | 50 | 50 | 50 |
| Fructose Richness (%) | 94.5 | 75.5 | 80.5 |
| Dextrose Richness (%) | 2 | 6.6 | 5.4 |
| Allulose Richness (%) | 1 | 2.1 | 1.7 |
| Di-Allulose Richness (%) | 1 | 10.9 | 8.3 |
| Other Richness (%) | 1.5 | 4.9 | 4.1 |
| Step 2/Step 3 | Stream 2/3/4 | Stream 17 | — |
| Flow rate by mass (kg/h) | 1324 | 41 | — |
| Dry Matter (%) | 50 | 50 | — |
| Step 4 | Stream 4' | Stream 14 | Stream 5 |
| Flow rate by mass (kg/h) | 1673 | 2061 | 2993 |
| Dry Matter (%) | 50.2 | 26.2 | 10 |
| Fructose Richness (%) | 49.6 | 75.5 | 2.8 |
| Dextrose Richness (%) | 4.5 | 6.6 | 0.6 |
| Allulose Richness (%) | 33.4 | 2.1 | 90.1 |
| Di-Allulose Richness (%) | 8.3 | 10.9 | 3.5 |
| Other Richness (%) | 4.2 | 4.9 | 3 |
| Step 5 | Stream 5 | Stream 6 | Stream 12 |
| Flow rate by mass (kg/h) | 2993 | 2797 | 196 |
| Dry Matter (%) | 10 | 8.7 | 29 |
| Fructose Richness (%) | 2.8 | 2.7 | 3 |
| Dextrose Richness (%) | 0.6 | 0.6 | 0.7 |
| Allulose Richness (%) | 90.1 | 94.4 | 71.7 |
| Di-Allulose Richness (%) | 3.5 | 0.4 | 16.6 |
| Other Richness (%) | 3 | 1.9 | 8 |

TABLE 1b

Flow rates and composition of the Streams of steps 6 to 9 of Example 1

| Step/Characteristic | Stream | | |
|---|---|---|---|
| Step 6 | Stream 6 | Stream 7 | — |
| Flow rate by mass (kg/h) | 2797 | 279 | — |
| Dry Matter (%) | 8.7 | 87 | — |
| Fructose Richness (%) | 2.7 | 2.7 | — |
| Dextrose Richness (%) | 0.6 | 0.6 | — |
| Allulose Richness (%) | 94.4 | 93.7 | — |
| Di-Allulose Richness (%) | 0.4 | 1.1 | — |
| Other Richness (%) | 1.9 | 1.9 | — |
| Step 7a/7b | Stream 7/8/9 | | |
| Flow rate by mass (kg/h) | 279 | — | — |
| Dry Matter (%) | 87 | — | — |
| Step 8 | Stream 9 | Stream 10 | Stream 13 |
| Flow rate by mass (kg/h) | 279 | 126 | 152 |
| Dry Matter (%) | 87 | 97 | 76.5 |
| Fructose Richness (%) | 2.7 | 0.1 | 5.4 |
| Dextrose Richness (%) | 0.6 | 0 | 1.2 |
| Allulose Richness (%) | 93.7 | 99.7 | 87.5 |
| Di-Allulose Richness (%) | 1.1 | 0.2 | 2.2 |
| Other Richness (%) | 1.9 | 0 | 3.7 |
| Step 9 | Stream 10 | Stream 11 | — |
| Flow rate by mass (kg/h) | 126 | 122 | — |
| Dry Matter (%) | 97 | 99.8 | — |

Step 3:

Stream 3 is demineralized by passing it over a Dowex 88 strong cationic resin and then a Dowex 66 weak anionic resin at a mean flow rate of 2 BV/h. The carboys are maintained at a temperature of 45° C. and the resistivity of Stream 4 at the end of the demineralization remains greater than 100 kΩ·cm$^{-1}$ at the outlet (Stream 4). When this is not the case, the resins are regenerated.

Step 4:

Stream 4 is mixed with Stream 12 (nanofiltration retentate) and with Stream 13 (crystallization mother liquors) so as to form a Stream 4' which feeds the continuous simulated mobile bed (SMB) chromatography (SCC ARI® equipped with 8 columns) of the circuit. The mean feed flow rate is 1673 kg/h at 50% DM.

The chromatography parameters are defined as follows:
Volume/column: 2 m³
Resin: Dowex Monosphere 99Ca/320
Temperature: 60° C.
Flow rate water/Stream 4' (vol./vol.): 2.4
Load (Feed flow rate/resin volume): 0.09 h$^{-1}$ Two fractions are extracted: the raffinate of the SCC (Stream 14), and the fraction rich in D-allulose (Stream 5) which leaves for step 5. 7% of Stream 14 is flushed (Stream 15) in order to discharge the allulose dimers, while the remainder (Stream 16) leaves again for step 1 after having been brought to a dry matter content of 50% by means of an evaporator.

crystallization and to form the massecuite. The water condensed during this stage is continuously reinjected along the walls at the top of the crystallizer.

The various Streams during the evaporative cooling stage in the adiabatic crystallizer-evaporator under vacuum is reported in Table 2.

TABLE 2

Characteristics of the various Streams in the adiabatic crystallizer-evaporator under vacuum

| Parameter | Stream 7 | Stream 7a) | Stream 7b) | Stream 7c) | Stream 7d) | Stream 8 |
| --- | --- | --- | --- | --- | --- | --- |
| Flow rate by mass (kg/h) | 279 | 519 | 798 | 1203 | 405 | 279 |
| Dry Matter (%) | 87 | 83 | 84.1 | 85.1 | 87 | 87 |
| Temperature (° C.) | 68.3 | 35 | 46 | 42.4 | 35 | 35 |

Step 5:

Stream 5 is treated on batchwise-mode nanofiltration equipment. The parameters are as follows:
Transmembrane pressure: 30 bar
Temperature: 20° C.
Membrane: GE Duracon NF1 8040C35
Volume Concentration Factor (VCF): 16

Figure 6:
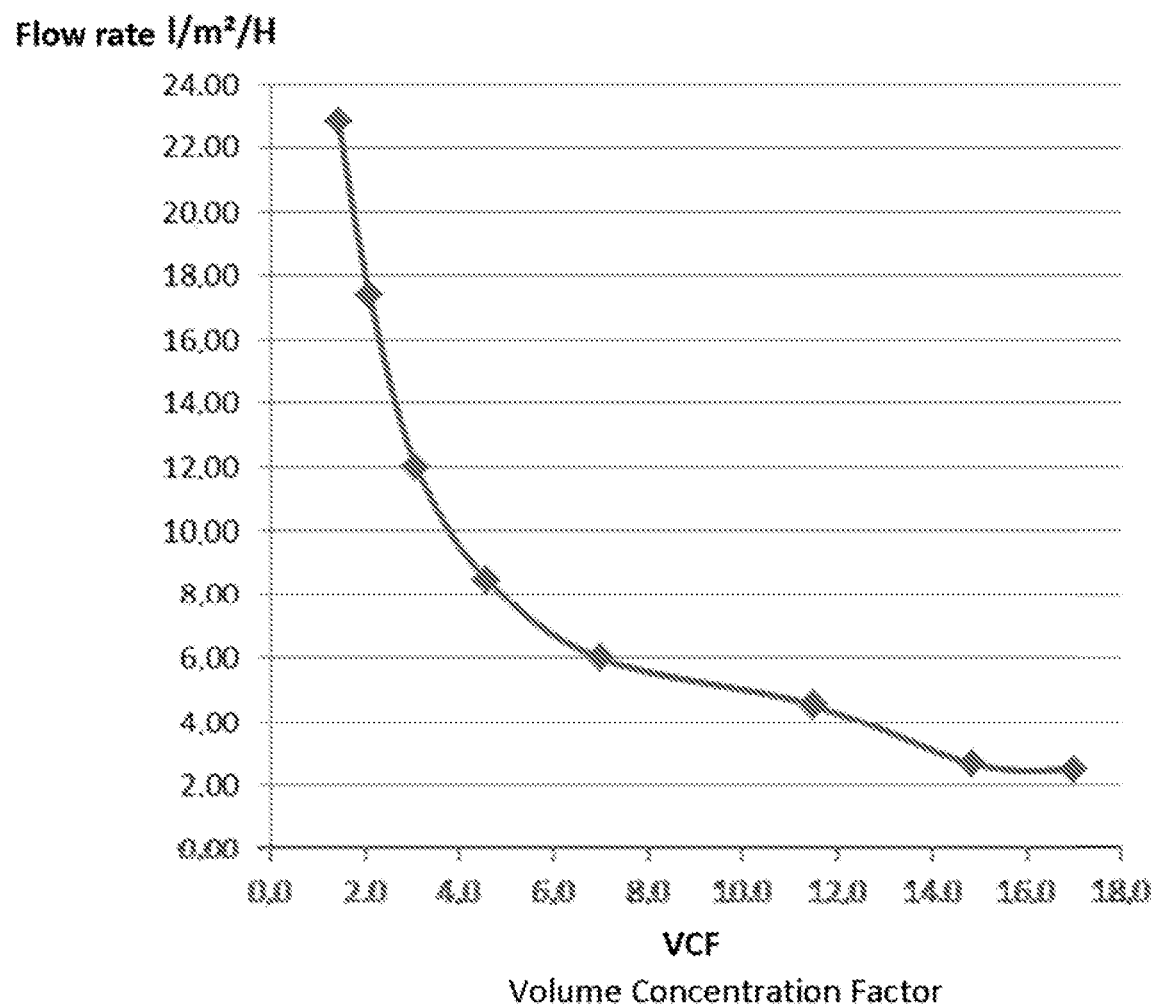
FIG. 6 represents the curve of permeation relative to the nanofiltration step, that is to say the flow rate as a function of the volume concentration factor.
Figure 7:
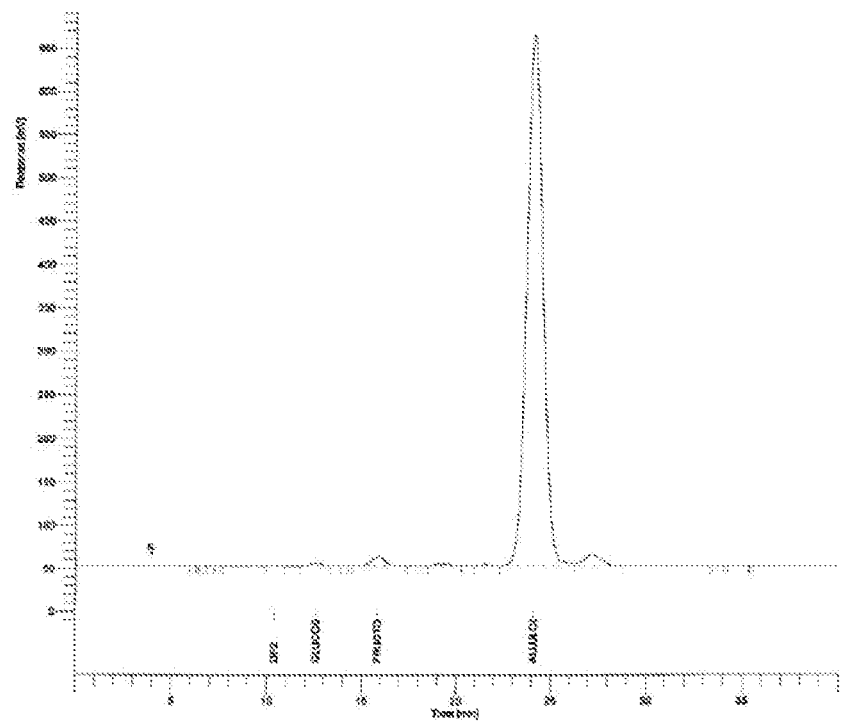
FIG. 7 represents an HPLC chromatogram of a D-allulose-rich composition sampled in the process of the invention (see FIG. 3), that is to say before nanofiltration.
Figure 8:
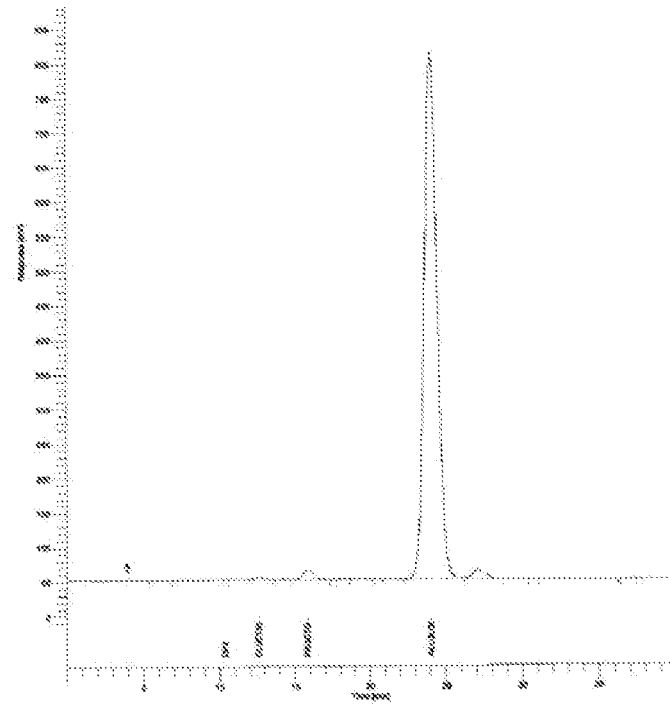
FIG. 8 represents an HPLC chromatogram of a permeate sampled in the process of the invention (see FIG. 3), that is to say after nanofiltration.
Figure 9:
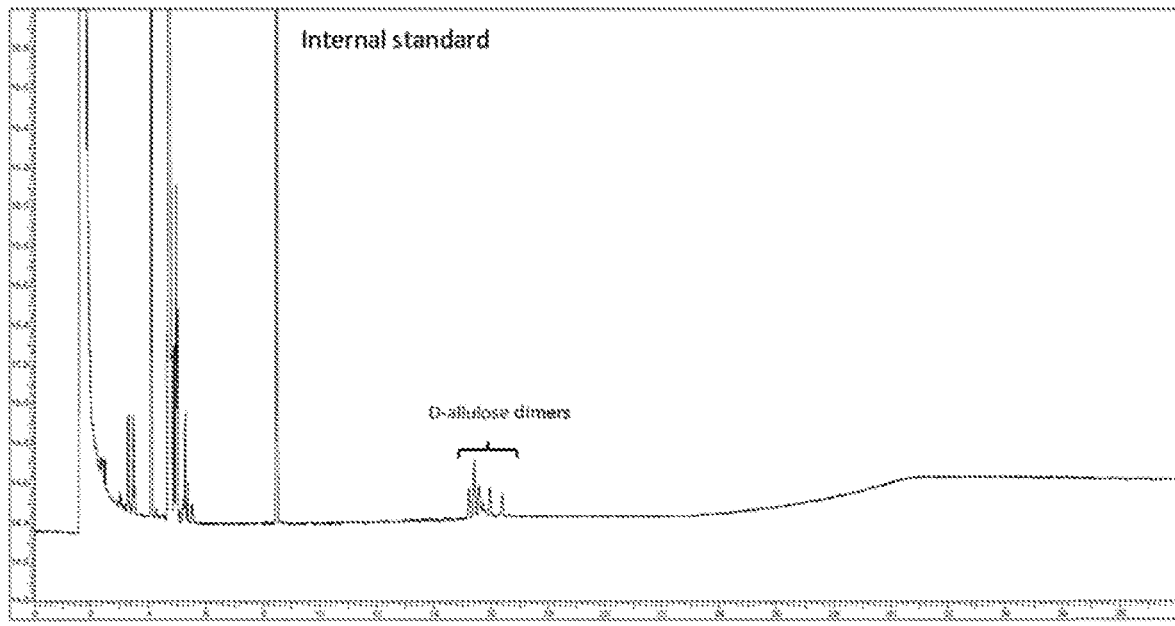
FIG. 9 represents a GC chromatogram, in the zone characteristic of the dimers, of a D-allulose-rich composition sampled in the process of the invention (see FIG. 3), that is to say before nanofiltration.
Figure 10:
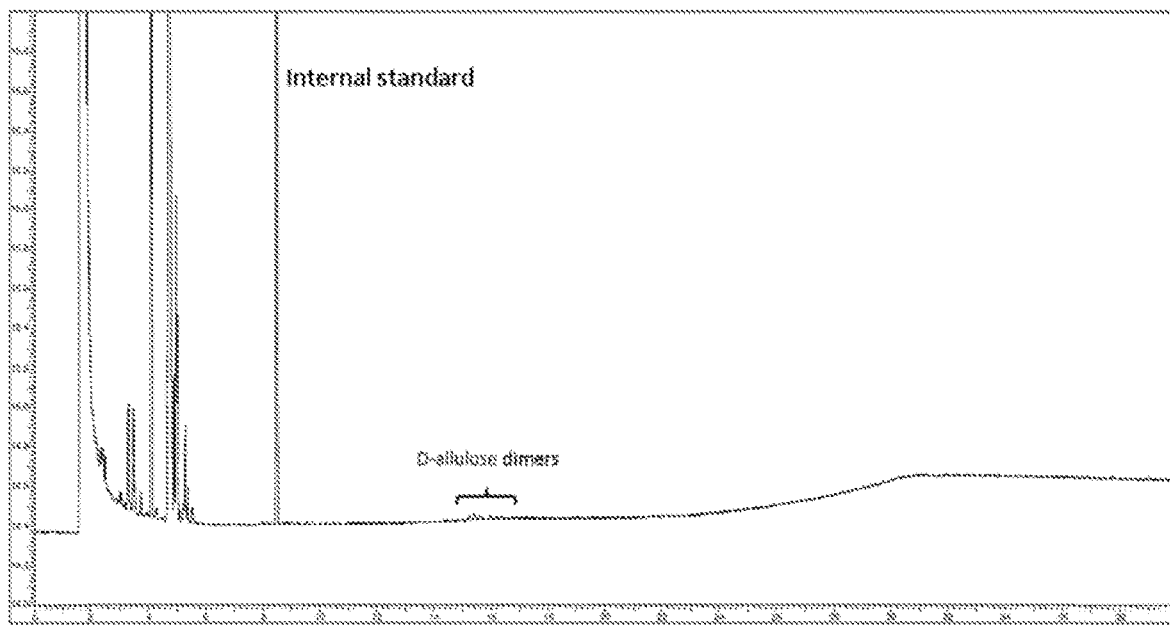
FIG. 10 represents a GC chromatogram, in the zone characteristic of the dimers, of a permeate sampled in the process of the invention (see FIG. 3), that is to say after nanofiltration.

The allulose dimers become concentrated in the retentate (Stream 12) and this retentate is recycled and mixed with Stream 4, whereas the permeate (Stream 6) is recovered. FIG. 6 gives the details of the permeation of the syrups as a function of the VCF.

Step 6:

Stream 6 passes through a two-stage evaporator, the pressure of which is below 50 mbar. On leaving the first stage, the Stream is at a temperature of 38° C. and has a dry matter content of 35%. On leaving the second stage, the Stream reaches a temperature of 48° C. and has a dry matter content of 87%. The stock solution of D-allulose (Stream 7) is obtained at the end of this step.

Step 7a:

The stock solution thus formed (Stream 7) is introduced immediately after having been heated to 68° C. by an exchanger into an adiabatic crystallizer-evaporator under vacuum, with a working volume of 3 m³, inside which the pressure is maintained at 35 mbar.

Figure 4:
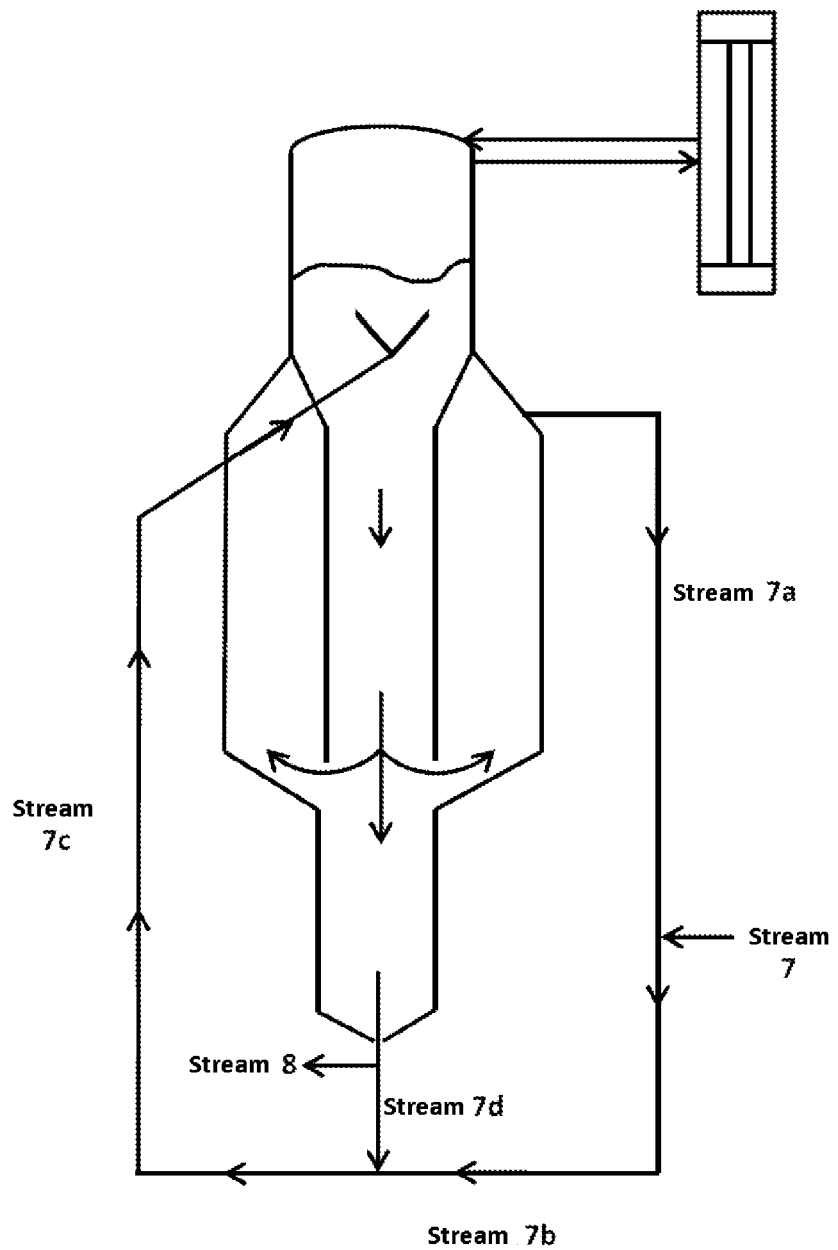
FIG. 4 represents an example of an adiabatic crystallizer-evaporator under vacuum, of use in a variant of the process of the invention.

The operating principle of the adiabatic crystallizer-evaporator under vacuum that is used here is described in detail in FIG. 4:

Stream 7a is composed of supersaturated D-allulose syrup at 35° C. and finest D-allulose particles. It is mixed with Stream 7 in a ratio such that the mixture is just below the limit of solubility of the mixture (84% dry matter and 46° C.) (Stream 7b). The fine particles are thus remelted.

The massecuite is withdrawn from the adiabatic crystallizer-evaporator at a temperature of 35° C., at the same rate as the mixture, so as to keep the level constant in the adiabatic crystallizer-evaporator. This massecuite recovered is separated into two streams: Stream 7d and Stream 8. Stream 7d is entrained with Stream 7b so as to form a Stream 7c comprising the stock solution of D-allulose and also initiators for the crystallization. The mixture ratio is formed in such a way as to again be beyond the solubility (85.5% dry matter and 42.7° C.) so that the crystals can continue their growth.

Stream 7c is thus introduced into the adiabatic crystallizer-evaporator under vacuum so as to prolong the Step 7b:

The massecuite withdrawn is injected at the top of the vertical crystallizer which has a working volume of 8 m³ and is equipped with a stirrer and also with five cooling layers. The massecuite is brought from 35 to 20° C. over the course of 40 h, that is to say a cooling gradient of approximately 0.4° C./h. The crystallizer diagram is presented in FIG. 5. The temperature of the cooling water in the layers is the following:

1. 34° C. at inlet, 32° C. at outlet
2. 31° C. at inlet, 29° C. at outlet
3. 28° C. at inlet, 26° C. at outlet
4. 25° C. at inlet, 22° C. at outlet
5. 21° C. at inlet, 20° C. at outlet Step 8:

At the bottom of the crystallizer, the suspension of crystals (Stream 9) is recovered and then centrifuged on a Rousselet Robatel SC 100KSA centrifugal dryer. The crystal suspension is systematically centrifugable, which means that the process is very stable over time. The mother liquors (Stream 13) are recycled and mixed with Streams 4 and 12. The wet D-allulose crystals are recovered (Stream 10). A first clarification with water and then a final clarification with ethanol of about 0.5% m/m is carried out in order to improve the separation. The clarified crystals comprise 3% of water.

Step 9:

The wet crystals pass through a rotary dryer and dried crystals which comprise 0.4% of water are obtained. A final cooling in a fluidized bed lowers the temperature of the crystals from 60 to 25° C. The final crystals are recovered (Stream 11) and then packaged. The overall yield of D-allulose crystals, which is the ratio, expressed by dry mass, of the mass of D-allulose crystals obtained to the mass of D-fructose introduced, is 72%.

Example 2

Example 2 is identical to Example 1 with the difference that no recycling is carried out. Stream 7 comprises 0.7% of D-allulose dimers. The suspension of crystals of Stream 9 is always centrifugable over time. Although the overall yield of crystals is only 12%, the process has the advantage of being stable, contrary to the processes of the comparative examples, not using the nanofiltration step, that will be presented below.

Comparative Example 1

Comparative example 1 is identical to Example 1, with the difference:
- that no nanofiltration step is carried out,
- that no mother liquor recycling step is carried out,
- that the recycling of the raffinate (Stream 14) is recycled in its entirety so as to be mixed with Stream 1 of the D-fructose syrup,
- that the crystallizing step is carried out as follows: the stock solution formed (Stream 7) is introduced sequentially into three vertical crystallizers with a working volume of 8 m³ identical to that used for the crystallizing step 7b of Example 1. The cooling gradient is 0.33° C./h to 20° C. An initiator of D-allulose having a D4,3 approximately equal to 60 μm is introduced into each crystallizer in mass amounts of 0.1%, this amount being expressed relative to the dry weight of D-allulose introduced into the crystallizer.

Figure 1:
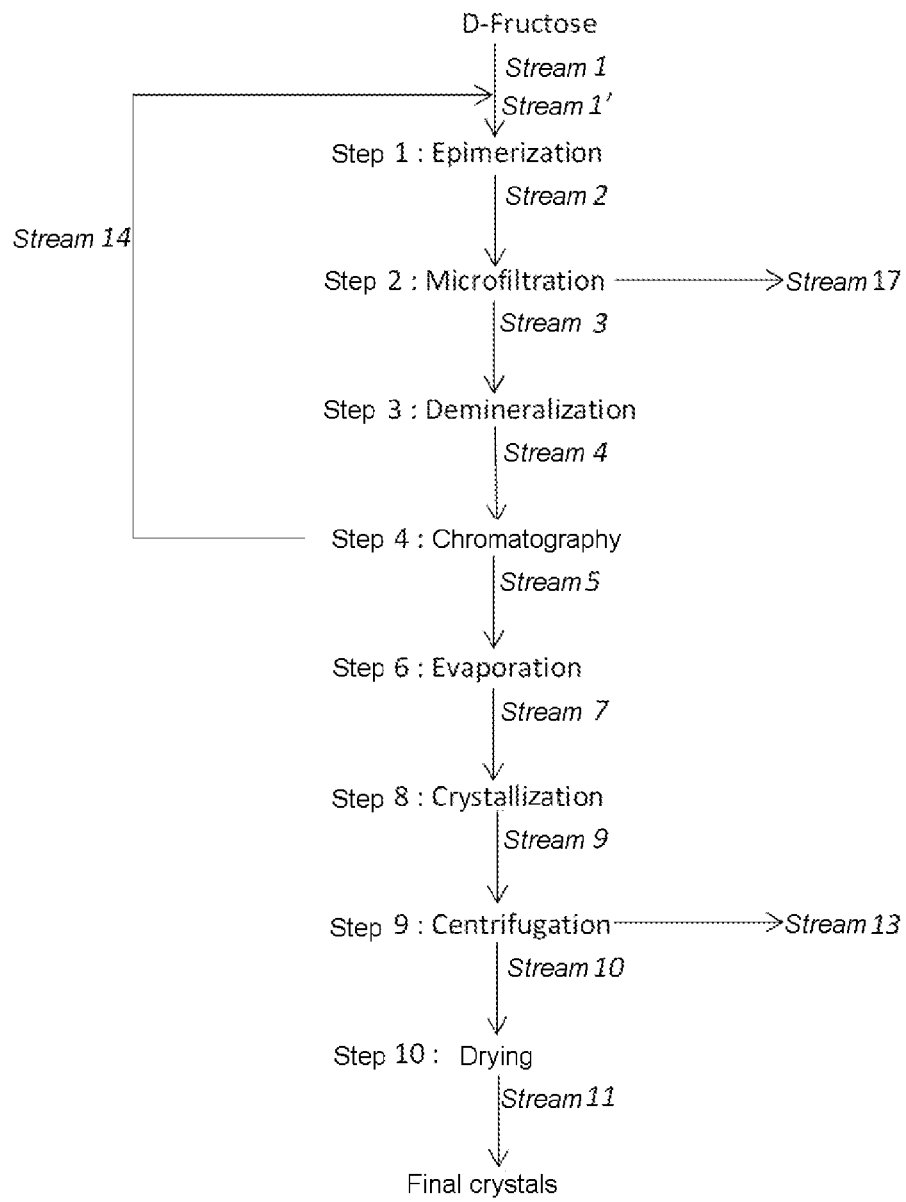
FIG. 1 represents diagrammatically a circuit for producing D-allulose crystals in which the D-fructose-rich chromatography raffinate is recycled so as to be mixed with the fructose at the top of the epimerization reaction.

The production circuit used (i.e the various steps of the process used) is that corresponding to FIG. 1.

Stream 7 comprises 1.9% of D-allulose dimers. A Stream 9 is recovered and is taken to step 8. This Stream 9 is a massecuite which is not always centrifugable. At the end of one week, Stream 7 comprises 2.2% of D-allulose dimers, and the massecuite of Stream 9 even becomes systematically non-centrifugable (crystals too small in size).

Comparative Example 2

Comparative example 2 is identical to Comparative example 1, with the difference that the mother liquors are totally recycled (Stream 13) so as to be mixed with the composition rich in D-allulose resulting from the chromatography step (Stream 5) and that the raffinate (Stream 14) is not recycled and is flushed from the circuit.

Figure 2:
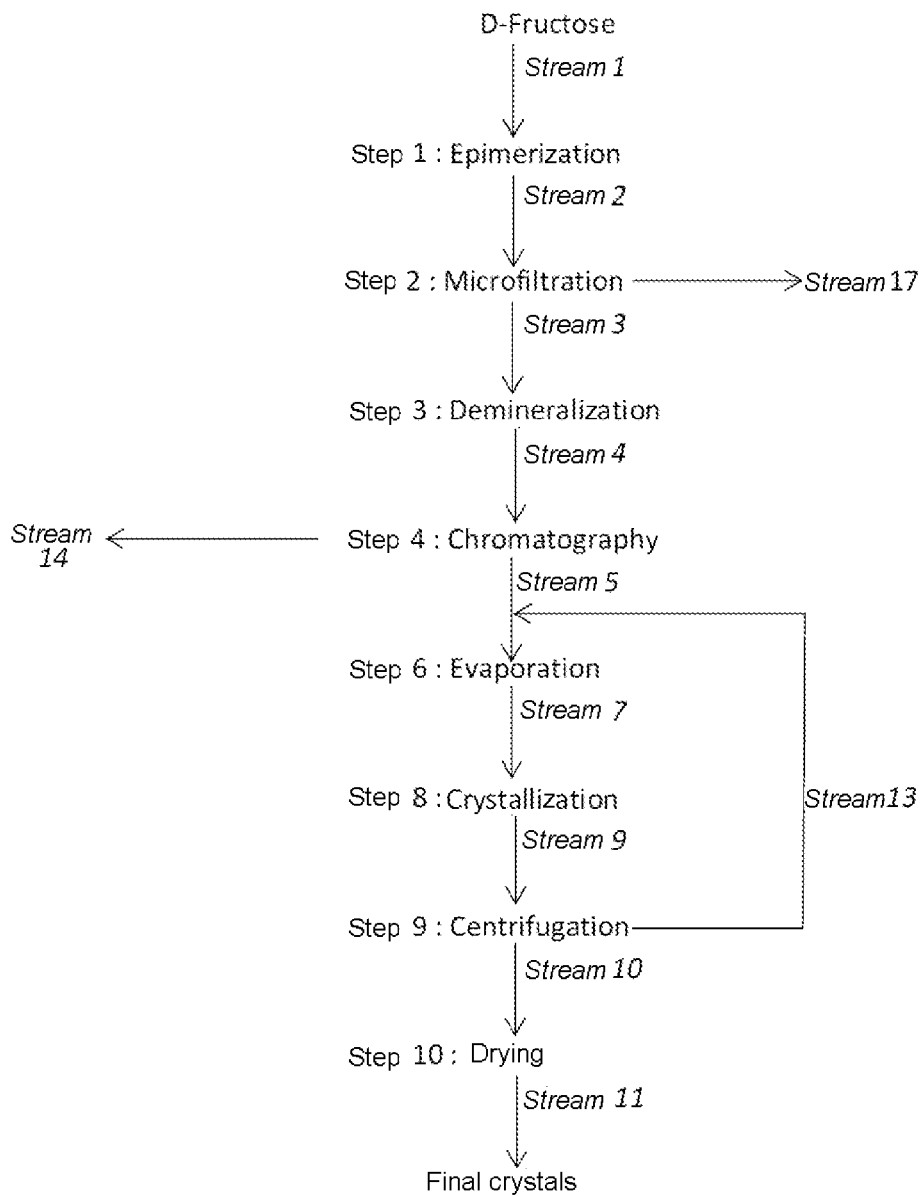
FIG. 2 represents diagrammatically a circuit for producing D-allulose crystals in which the crystallization mother liquors are recycled so as to be mixed with the D-fructose/D-allulose composition resulting from the epimerization reaction.

The production circuit used is that corresponding to FIG. 2.

Stream 7 comprises 1.9% of D-allulose dimers. A Stream 9 is recovered and is taken to step 8. This Stream 9 is a massecuite which is not always centrifugable. From the moment the mother liquors are recycled, Stream 7 comprises 2.4% of D-allulose dimers, and the massecuite of Stream 9 even becomes systematically non-centrifugable (crystals too small in size).

Comparative Example 3

Comparative example 3 is identical to Comparative example 1, with the difference that the raffinate is not recycled.

The production circuit used is that corresponding to FIG. 1.

Stream 7 comprises 1.9% of D-allulose dimers. A Stream 9 is recovered and is taken to step 8. This Stream 9 is a massecuite which is not always centrifugable. When it is centrifugable, the mother liquors separate from the allulose crystals which can be recovered. However, sometimes, Stream 9 consists of a mass of small indissociable crystals, synonymous with spontaneous nucleation in the crystallizer. In that case, it is necessary to empty the Stream out of the circuit. This makes the process industrially unexploitable.

The summary of the results obtained for these processes is reported in Table 3. The overall reported yield is an average over one week of use.

The characteristics of the crystals obtained for Examples 1 and 2 and Comparative example 3, and also the D-allulose crystals sold by the company CJ Cheiljedang Food Ingredient, are reported in Table 4.

TABLE 3

| | | Comparison of the various circuits tested | | | |
|---|---|---|---|---|---|
| Example | Circuit | Recycling of Stream 14 (%) | Recycling of Stream 13 (%) | Recycling of Stream 12 (%) | Overall yield of D-allulose crystals of the continuous process |
| Comparative example 1 | FIG. 1 | 100 | 0 | 0 (no nanofiltration) | Unstable then stopping of facility, does not operate continuously |
| Comparative example 2 | FIG. 2 | 0 | 100 | 0 (No nanofiltration) | Unstable then stopping of facility, does not operate continuously |
| Comparative example 3 | FIG. 1 | 0 | 0 | 0 (no nanofiltration) | Unstable, does not operate continuously |
| Example 1 | FIG. 3 | 93 | 100 | 100 | Stable, 72% |
| Example 2 | FIG. 3 | 0 | 0 | 0 | Stable, 12% |

The process of the invention makes it possible to obtain a crystallization that is stable over time, which is demonstrated in the industrial process exemplified above (Examples 1 and 2). It also makes it possible to perform very substantial recyclings and thus increase the overall yield of D-allulose crystals (see Example 2). By performing recyclings without being sure to separate the D-allulose dimers by means of the nanofiltration step, the illustrative Comparative examples 1 and 2 above demonstrated that the industrial crystallization process had to be stopped because the massecuite systematically becomes non-centrifugable (crystals too small in size).

TABLE 4

| | Characteristics of the crystals obtained | | | | |
|---|---|---|---|---|---|
| Crystals | Residual moisture content | D4, 3 (μm) | % D-allulose dimers (GC) | Feret min/Feret max at 200 μm | Feret min/Feret max at 400 μm |
| Example 1 | 0.3% | 302 | 0.2% | 0.63 | 0.68 |
| Example 2 | 0.3% | 285 | <0.1% | 0.68 | 0.76 |
| Comparative example 3 | 0.3% | 297 | 0.7% | 0.55 | 0.53 |
| Crystals sold by CJ Cheiljedang Food Ingredient | 0.5% | 346 | 0.7% | 0.53 | 0.50 |

Figure 14:
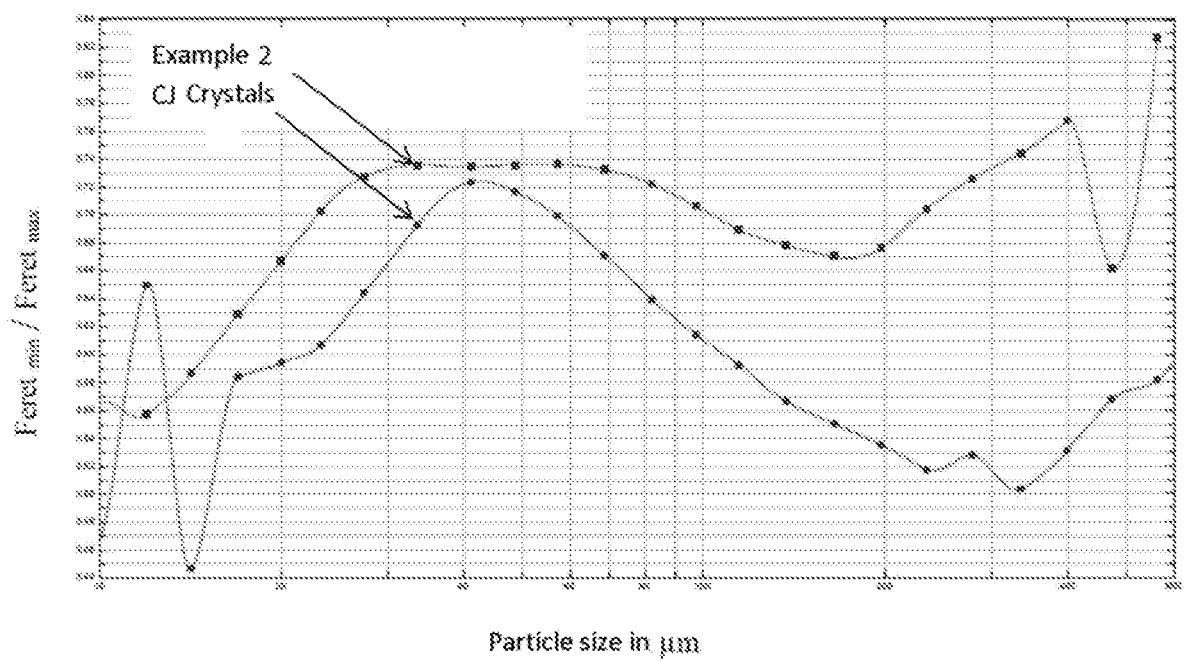
FIG. 14 represents the ratio of the diameters Feret min/Feret max as a function of the volume particle sizes D4,3 for two types of D-allulose crystals.

FIG. 14, which represents, for the D-allulose crystals of Example 2 and the D-allulose crystals sold by CJ, the ratio of the Feret min/Feret max diameters as a function of the volume particle sizes D4,3, demonstrates that it is for the populations of large size, greater than or equal to 200 μm (for example in the range of from 200 to 400 μm), that clear differences in appearance are observed between the crystals according to the invention and the comparative crystals. Thus, in this range of from 200 to 400 μm, the Feret min/Feret max ratios are, for the comparative crystals, always less than 0.55, whereas the crystals according to the invention have a ratio of at least 0.63. This difference is entirely in agreement with the optical microscopy images of FIGS. 11 and 12, which demonstrate visually that the crystals according to the invention have a much more squat appearance than the comparative crystals. With regard to the CJ crystals of FIG. 13 (optical microscopy images), it is noted that they are non-individualized needle-shaped crystals.

Although comparative example 3 is not strictly identical to the teaching of document WO 2011/119004 A2 with regard to the concentration step (in particular in that the applicant succeeded in carrying out the concentration step more optimally, so as to further reduce the amount of D-allulose dimers formed), the crystals obtained use a process of the same type as that used to produce the crystals described in example 6 of document WO 2011/119004 A2 (in particular with regard to the crystallization which was carried out exclusively by controlled cooling in water). This comparative test 3, producing crystals comprising 0.7% of D-allulose dimers, therefore demonstrates well that document WO 2011/119004 A2 does not make it possible to form the crystals of the invention.

Use of the Crystals of the Invention in Various Applications

The crystals of Example 2 were used in the production of products which follow.

Production of Meal Replacement Drinks

The objective is to create a powdered meal replacement drink comprising few calories. This powdered drink must be able to exhibit good flow and form few lumps when it is formulated.

Formula:

| | Percentages | |
|---|---|---|
| Ingredients | Allulose | Sucrose |
| Sugar | 28.29 | 28.29 |
| Milk protein concentrate | 26.62 | 26.62 |
| GLUCIDEX ® 19 maltodextrin | 22.63 | 22.63 |
| NUTRIOSE ® FM 06 Soluble fiber | 10.82 | 10.82 |
| Pea protein | 9.98 | 9.98 |
| Sodium caseinate | 0.67 | 0.67 |
| Vanilla cream flavor | 0.50 | 0.50 |
| Vanilla flavor | 0.33 | 0.33 |
| Cekol 10000 | 0.17 | 0.17 |
| Total | 100.00 | 100.00 |

After having been weighed out, the ingredients are vigourously mixed in a dry mixer. The drink is then easily reconstituted by adding 210 g of water to 30 g of formula, without forming lumps. The formula using the crystals of the invention has a flow behavior entirely similar to the formula comprising sucrose, while at the same time comprising many fewer calories.

Production of Yellow Cake

The objective is to provide a yellow cake having a satisfactory texture and appearance, the calorie content of which is reduced by 25%.

Formula:

| Ingredients | Reference | Invention |
|---|---|---|
| Sucrose | 24.10 | 0.00 |
| Cake flour | 27.09 | 25.24 |
| Nutriose ® FB06 | 0.0 | 1.75 |
| Egg yolk | 10.00 | 10.00 |
| Butter | 15.45 | 15.45 |
| Milk | 21.81 | 21.81 |
| Salt | 0.25 | 0.25 |
| Chemical yeast | 0.80 | 0.90 |
| Vanilla | 0.50 | 0.50 |
| Allulose | 0.00 | 24.10 |
| Total | 100.00 | 100.00 |

Method:
1. Mix the flour, salt, Nutriose® and yeast.
2. Cream the butter with the sucrose or the allulose.
3. Add the egg yolk and the vanilla to the cream and then add the milk so as to form a creamy mixture.
4. Add the mixture comprising the flour to the creamy mixture and mix in a mixer in the slow setting (1 minute) then more vigourously until the formula is well mixed.
5. Pour 600 g of the paste into a 9-inch greased circular mold.
6. Bake at 180° C. for 20 minutes.

The objective is achieved: the cake using the crystals of the invention has a very pleasant texture in the mouth (the term "crumb texture" is used) and the cake keeps its shape after baking.

Production of Chocolate Cookies

The following formulas were prepared:

| Ingredients | Reference | Allulose | Allulose + Nutriose ® |
|---|---|---|---|
| Wheat flour | 25 | 25 | 23 |
| Sodium bicarbonate | 0.14 | 0.14 | 0.14 |
| Salt | 0.17 | 0.17 | 0.17 |
| Melted butter | 14.16 | 14.16 | 14.16 |
| Nutriose ® FB06 | 0 | 0 | 2 |
| Allulose | 0 | 29.17 | 29.17 |
| Brown sugar | 20.35 | 0 | 0 |
| Caster sugar | 8.82 | 0 | 0 |
| Vanilla | 1.14 | 1.14 | 1.14 |
| Eggs | 7 | 7 | 7 |
| Chocolate chips | 23.22 | 23.22 | 23.22 |
| Total | 100 | 100 | 100 |

Method:
1. Mix the dry ingredients together.
2. Cream the butter with the sugars or the allulose.
3. Add the eggs and the vanilla to the creamy mixture.
4. Add the mixture comprising the flour to the creamy mixture and mix in a mixer in the slow setting (1 minute) then more vigourously until the formula is well mixed.
5. Add the chocolate chips and mix.
6. Weigh out portions of 30 g and bake at 160° C. for 8 minutes.

The allulose-based cookie dough (column 2) spreads less than the sugar-based dough (column 1). However, the dough of column 3 spreads in the same way as the dough of column 1.

During baking, the allulose-based cookies brown more rapidly.

It should be noted that the cookies have a dome shape. The height of the cookie according to the invention is less swollen and said cookie does not collapse after baking, unlike the sugar-based cookie, thereby allowing it to keep a better appearance.

The allulose-based cookies have a good, although less sweet, taste. The texture of the cookies according to the invention is soft and more moist than the sugar-based cookies.

The water activity (w a) and the moisture content (M) of the cookies is measured over time:

The allulose-based cookies exhibit better stability with respect to moisture.

Production of Oat Flake Cookies

| | Formulas | |
|---|---|---|
| Ingredients | Reference | Invention |
| Wheat flour | 16.84 | 15.09 |
| Nutriose ® FB06 | 0.00 | 1.75 |
| Sodium bicarbonate | 0.42 | 0.42 |
| Yeast | 0.27 | 0.27 |
| Salt | 0.44 | 0.44 |
| Butter | 14.53 | 14.53 |
| Sucrose | 14.08 | 11.30 |
| Brown sugar | 13.89 | 0.00 |
| Allulose | 0.00 | 16.67 |
| Eggs | 6.43 | 6.43 |
| Vanilla | 0.60 | 0.60 |
| Oat flakes | 19.35 | 19.35 |
| Inclusions* | 13.15 | 13.15 |
| Total | 100.00 | 100.00 |

*The inclusions comprise 50.0 grams of pecan nuts, 20.0 grams of cranberries and 18.6 grams of blueberries.

Method:
1. Mix the flour, the Nutriose®, the sodium bicarbonate, the yeast and the salt.
2. Cream the butter with the sugars or the allulose.
3. Add the eggs and the vanilla to the creamy mixture.
4. Add the mixture comprising the flour to the creamy mixture and mix in a mixer in the slow setting (1 minute) then more vigourously until the formula is well mixed.
5. Add the oat flakes and mix.
6. Add the inclusions and mix.
7. Weigh out portions of 30 g and bake at 160° C. for 10 minutes.

The cookies obtained using allulose instead of sugar are slightly browner and have a crunchy texture after baking.

Production of Bubblegum

A bubblegum was produced with the recipe below:

| Ingredients | Parts |
|---|---|
| Flama T gum base | 24 |
| Allulose | 50 |
| Lycasin ® 85/55 | 10 |
| Nutriose ® FB06 | 13.4 |
| Liquid flavoring | 0.9 |
| Powdered flavoring | 1.2 |
| Acidifier | 0.5 |
| Total | 100 |

The bubblegum has an entirely satisfactory appearance, similar to commercial bubblegums.

| | Reference | | Allulose | | Allulose + Nutriose ® | |
|---|---|---|---|---|---|---|
| Date | w a | Moisture content (%) | w a | Moisture content (%) | w a | Moisture content (%) |
| Day 1 | 0.6429 | 7.62 | 0.5482 | 8.91 | 0.5027 | 8.69 |
| Day 7 | 0.7531 | 9.42 | 0.5859 | 9.59 | 0.5472 | 8.82 |
| Day 30 | 0.7633 | 8.33 | 0.5888 | 9.47 | 0.5563 | 9.11 |

The invention claimed is:

1. Process for producing D-allulose crystals comprising:
a step of providing a composition rich in D-allulose;
at least one nanofiltration step of said composition rich in D-allulose so as to provide a retentate and a permeate, said nanofiltration step being performed with a membrane having a cut-off threshold of less than 300 Da;
a step of recovering the nanofiltration permeate;
a step of concentrating said permeate so as to form a stock solution to be crystallized;
a step of crystallizing the stock solution so as to form D-allulose crystals and mother liquors.

2. Process according to claim 1, wherein the stock solution obtained comprises by dry mass:
from 80% to 99% of D-allulose,
from 0% to 20% of D-fructose,
from 0% to 10% of glucose,
from 0% to 1.5% of D-allulose dimers.

3. Process according to claim 1, wherein the volume concentration factor of the nanofiltration ranges from 5 to 20.

4. Process according to claim 1, wherein the crystallizing step comprises:
i. an adiabatic evaporative cooling stage, carried out in an adiabatic crystallizer-evaporator under vacuum so as to form a massecuite,
ii. followed by a stage of crystallization by cooling of said massecuite so as to form crystals.

5. Process according to claim 4, wherein the temperature during the adiabatic evaporative cooling stage ranges from 30 to 40° C.

6. Process according to claim 1, wherein it is continuous.

7. Process according to claim 1, wherein it comprises at least one recycling step.

8. Process according to claim 1, wherein it comprises a step of recycling at least one part of the mother liquors.

9. Process according to claim 1, wherein it comprises a step of recycling at least one part of the retentate.

10. Process according to claim 1, wherein the step of providing the composition rich in D-allulose comprises:
a step of providing a composition comprising D-fructose;
an epimerizing step so as to form a composition comprising D-fructose and D-allulose;
a chromatography step so as to provide a composition rich in D-allulose and a composition rich in D-fructose.

11. Process according to claim 10, wherein it comprises a step of recycling at least one part of the composition rich in D-fructose.

12. Process according to claim 11, wherein the degree of recycling of the composition rich in D-fructose ranges from 50% to 95%.

13. D-allulose crystals comprising a mass content of D-allulose dimer, determined by gas chromatography (GC), of less than 0.50%, and having a volume mean size $D_{4,3}$ of greater than 200 μm, and for a given volume particle size $D_{4,3}$ chosen in the range of from 200 to 400 μm, a Feret min/Feret max ratio greater than 0.60.

14. D-allulose crystals according to claim 13, wherein they comprise a mass content of D-allulose dimer ranging from 0.01% to 0.48%.

15. D-allulose crystals according to claim 13, wherein they have this Feret min/Feret max ratio over all of the volume particle sizes $D_{4,3}$ in the range of from 200 to 400 μm.

* * * * *